US008465535B2

(12) United States Patent  (10) Patent No.: US 8,465,535 B2
Harris et al.  (45) Date of Patent: Jun. 18, 2013

(54) PORTABLE APPARATUS AND METHOD FOR THE ADMINISTRATION OF HEAT EXCHANGE IN THE LUNGS OF A MAMMAL

(75) Inventors: Steve B. Harris, Rancho Cucamonga, CA (US); Charles Platt, New York, NY (US); Gary Battiato, Boynton Beach, FL (US)

(73) Assignee: Critical Care Research, Inc., Rancho Cucamonga, CA (US)

( * ) Notice: Subject to any disclaimer, the term of this patent is extended or adjusted under 35 U.S.C. 154(b) by 326 days.

(21) Appl. No.: 12/733,908

(22) PCT Filed: Sep. 26, 2008

(86) PCT No.: PCT/US2008/011224
§ 371 (c)(1),
(2), (4) Date: Mar. 26, 2010

(87) PCT Pub. No.: WO2009/042220
PCT Pub. Date: Apr. 2, 2009

(65) Prior Publication Data
US 2011/0040359 A1  Feb. 17, 2011

Related U.S. Application Data

(60) Provisional application No. 60/995,499, filed on Sep. 27, 2007.

(51) Int. Cl.
*A61F 7/12* (2006.01)
*A61F 7/00* (2006.01)
(52) U.S. Cl.
USPC .......................................... 607/105; 607/113
(58) Field of Classification Search
USPC ....................................................... 607/105
See application file for complete search history.

(56) References Cited

U.S. PATENT DOCUMENTS

| | | | |
|---|---|---|---|
| 5,540,225 A * | 7/1996 | Schutt | 128/207.15 |
| 5,927,273 A | 7/1999 | Federowicz | |
| 5,957,880 A * | 9/1999 | Igo et al. | 604/6.11 |
| 6,149,624 A * | 11/2000 | McShane | 604/113 |
| 6,694,997 B2 | 2/2004 | Reyman | |
| 6,983,749 B2 * | 1/2006 | Kumar et al. | 128/204.15 |
| 7,422,601 B2 * | 9/2008 | Becker et al. | 607/105 |
| 2003/0131844 A1 | 7/2003 | Kumar | |
| 2003/0159700 A1 * | 8/2003 | Laufer et al. | 128/898 |
| 2005/0203598 A1 * | 9/2005 | Becker et al. | 607/105 |
| 2007/0162097 A9 * | 7/2007 | Rojas | 607/105 |
| 2007/0233212 A1 * | 10/2007 | Ginsburg et al. | 607/106 |
| 2008/0262377 A1 * | 10/2008 | Belson | 600/549 |
| 2009/0107491 A1 * | 4/2009 | Belson | 128/200.14 |
| 2009/0125087 A1 * | 5/2009 | Becker et al. | 607/113 |
| 2012/0080031 A1 * | 4/2012 | Belson | 128/203.15 |
| 2012/0226337 A1 * | 9/2012 | Tissier et al. | 607/105 |

* cited by examiner

*Primary Examiner* — Linda Dvorak
*Assistant Examiner* — Kaitlyn Smith
(74) *Attorney, Agent, or Firm* — Jay P. Hendrickson

(57) ABSTRACT

An apparatus and method for the delivery and removal of a biocompatible liquid to and from the lungs of a mammal, comprising an ice water container adapted for containing ice water; a biocompatible liquid tank disposed within the ice water container, with the tank adapted for containing a biocompatible liquid; and a biocompatible liquid infusion reservoir disposed within the biocompatible liquid tank. The apparatus also comprises a pump assembly and tube assembly that are in operable connection to the ice water container, biocompatible liquid tank and biocompatible liquid reservoir so as to provide a volume of biocompatible liquid to and from the lungs of a mammal, while breaths of oxygen are supplied using a manually operated air bag.

13 Claims, 21 Drawing Sheets

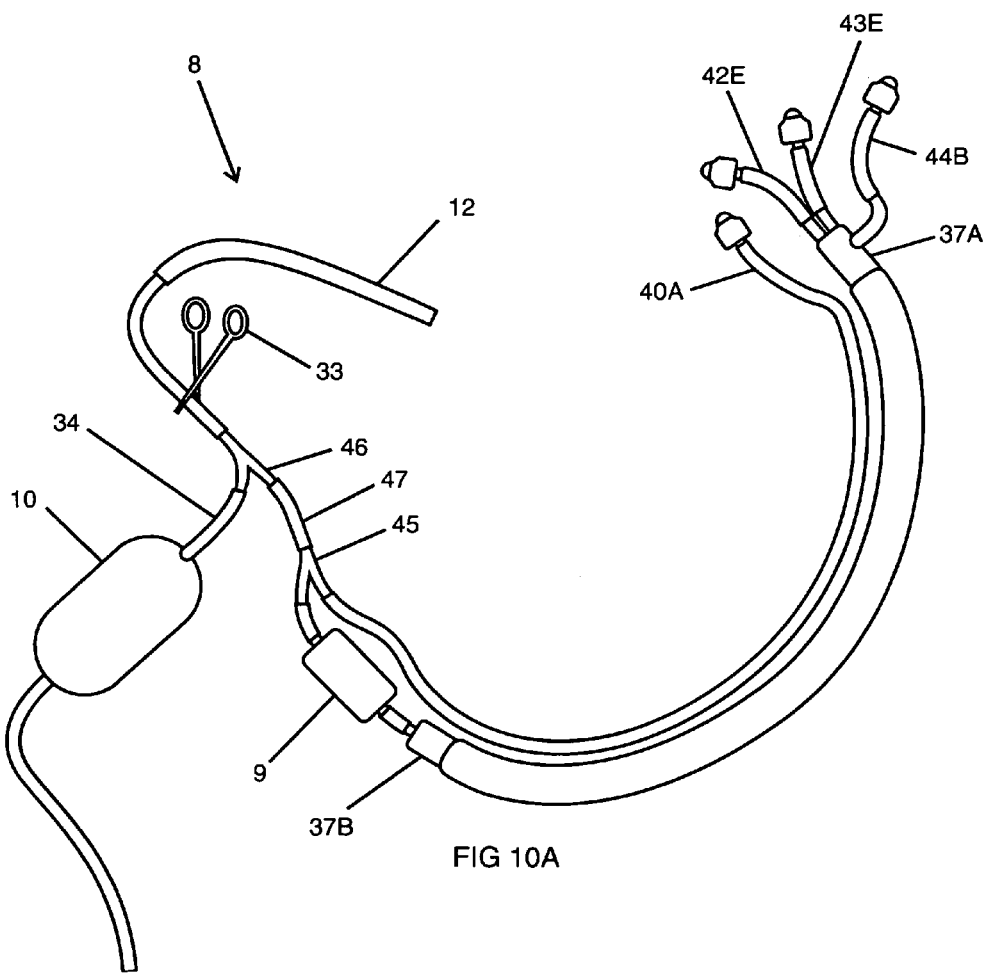
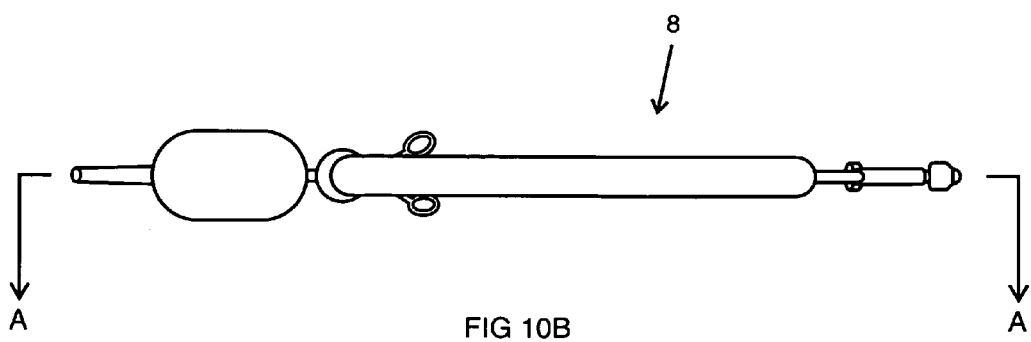
FIG 10A
FIG 10B

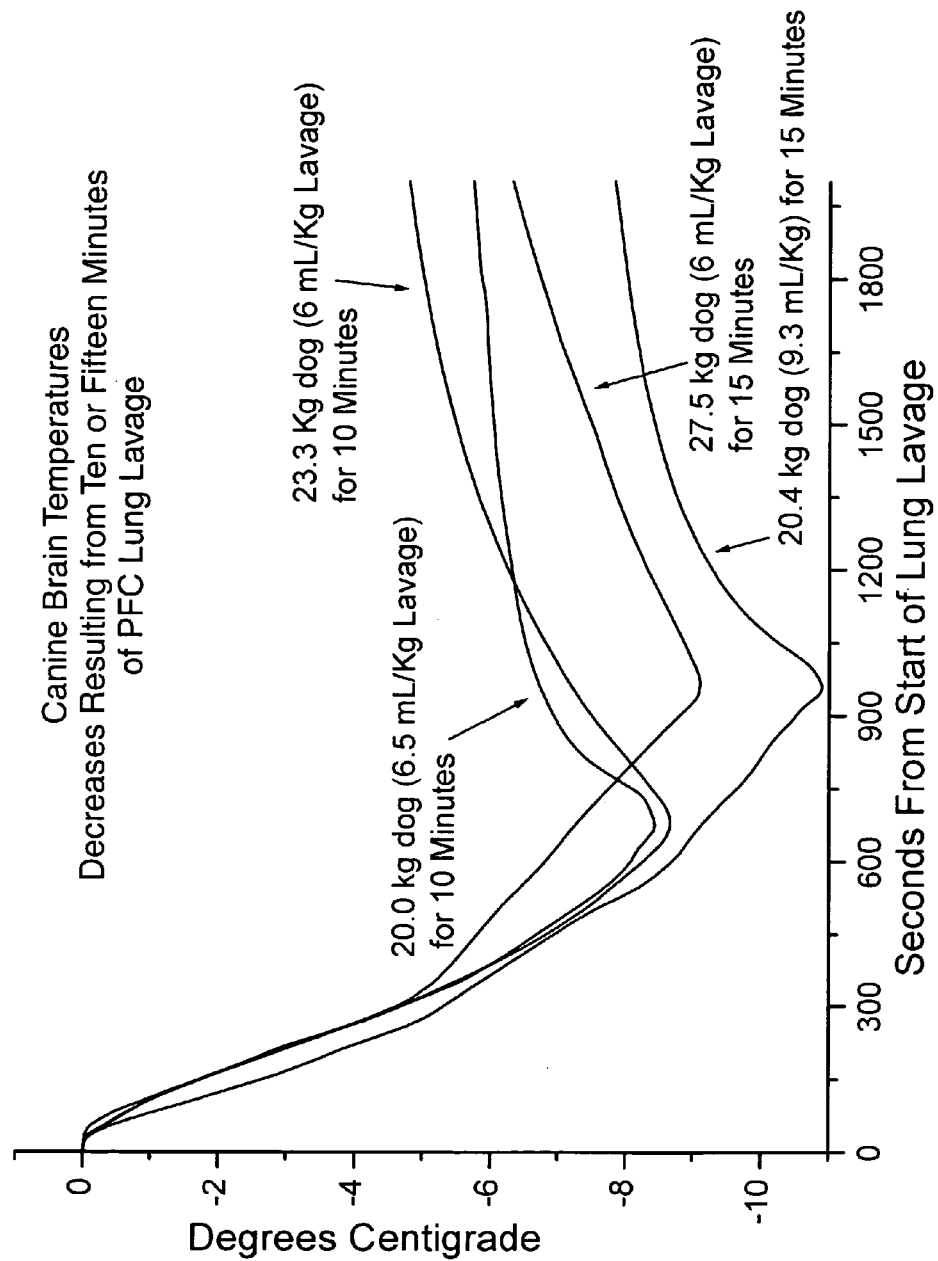

PORTABLE APPARATUS AND METHOD FOR THE ADMINISTRATION OF HEAT EXCHANGE IN THE LUNGS OF A MAMMAL

RELATED APPLICATION

This application is related to and claims the benefit under 35 U.S.C. §119(e) of U.S. Provisional Application No. 60/995,499, filed Sep. 27, 2007.

TECHNICAL FIELD

This application relates to devices for rapidly reversing hypothermia in mammals.

BACKGROUND

There are many situations in both human and veterinary medicine where it is desirable to rapidly reverse hyperthermia. There are also many clinical situations where it is essential to be able to rapidly reduce dangerously elevated body temperatures to near normal, as in the case of hyperthermia from heat stroke, drug or surgical anesthetic reaction, and febrile illness secondary to stroke, infection, or other illness. In fact, it has been demonstrated in several studies that patient mortality is directly dependent on the length of time a patient has a high body temperature, and inversely dependent on the rapidity with which core temperature is normalized. Further, it has been recently demonstrated that for patients suffering from post-resuscitation encephalopathy after recovery from a period of cardiac arrest, inducing hypothermia as an adjunct to other therapies after heartbeat is restored significantly increases survival rates and rates of discharge from hospital to functional living.

This application refers to and incorporates herein by reference U.S. Pat. No. 6,694,977, titled Mixed-Mode Liquid Ventilation Gas and Heat Exchange (hereinafter "MMLV patent"), in which a method of Mixed-Mode Liquid Ventilation ("MMLV") and a device ("Prior Device") for the administration of MMLV is disclosed for rapidly inducing or reversing hypothermia. The method comprises the continuous delivery and removal of perfluorocarbon to and from the lungs, while also providing for the delivery of gas breaths by means of a mechanical ventilator or other device at a rate that is independent of the delivery and removal of perfluorocarbon from the lungs. The inventors of the present apparatus have discovered, however, that when the purpose of the MMLV is to only induce hyperthermia in order to decrease core mammalian temperature, continuous delivery and removal of perfluorocarbon to and from the lungs need not be accompanied by the delivery of gas breaths that are independent of perfluorocarbon delivery and removal rates. Rather, the delivery of gas breaths can be synchronized with perfluorocarbon infusion or can be delivered at a rate independent of perfluorocarbon infusion. This discovery has, in part, lead to the development of a new apparatus and method for the administration of heat exchange in the lungs of a mammal that constitutes a substantial improvement over the prior heat exchange device and method disclosed in the MMLV patent.

Although the Prior Device has performed its functions well in the laboratory setting, its continual use over the years has revealed many undesirable features. One such limitation is that the Prior Device is cumbersome and not easily transported form one location to another due to the fact that the device consists of a perfluorocarbon tank containing perfluorocarbon, a separate vacuum reservoir tank to serve as a collection suction reservoir, a large peristaltic pump to infuse cold perfluorocarbon liquid, a vacuum pump to maintain the suction reservoir, a separate ice water tank containing ice water and a heat exchanger. Finally, the Prior Device contained a separate silicone membrane oxygenator unit, to add oxygen to the perfluorocarbon and remove carbon dioxide from it. In addition, due to the separation of the perfluorocarbon and the ice water tanks, long tubing must be utilized to transfer the perfluorocarbon from the perfluorocarbon tank to the heat exchanger where the perfluorocarbon is cooled before it is infused into the lungs of a patient. This results in an increase in the temperature of the perfluorocarbon during transit. Another difficulty that has been encountered with a later version of the Prior Device is that it utilizes a weighing system to meter the volume of perfluorocarbon contained within the perfluorocarbon tank and the weight is monitored using the LabView® program operating on a computer. This feature has proven to be overly complicated, failure-prone, heavy, and required a significant amount of electrical power. In yet another version of the Prior Device, which used no vacuum pumps but only peristaltic pumps, the apparatus used stepper motors to operate an infusion pinch valve to control the flow of perfluorocarbon to the patient, a suction pinch valve to control the flow of perfluorocarbon from the patient, and a recycling pinch valve to recycle the perfluorocarbon from the heat exchanger to the perfluorocarbon tank and back to the exchanger. Due to the nature of stepper motors they require a dedicated electronic circuit in order to operate the motors, which again added to the size, weight, complexity, and power consumption.

Another limitation of the Prior Device is that it was designed such that the infusion/suction tube was concentric with the endotracheal tube, and the end of the infusion tube was perforated in order to minimize potential damage to the lung tissue. These two features resulted in a substantial limitation on the volumes of perfluorocarbon that could be delivered to and removed from the lungs, and as result limited the rate of heat exchange in the lungs of canines to about 1.5° C. within 5 minutes. In addition the Prior Device used an occlusive pump for infusion and a large centrifugal pump to circulate ice water through a heat exchanger. Both pumps required 110v AC electrical current connections, were heavy, and were relatively inefficient. They were, therefore, unsuitable for applications requiring portability of the equipment. Previous versions of the apparatus also were used in conjunction with a mechanical ventilator, which was heavy, cumbersome, non-portable, and could not be coordinated with liquid infusion and removal.

Lastly, the Prior Device incorporated a gas exchanger to add oxygen to or remove carbon dioxide from the perfluorocarbon liquid, as would be appropriate for total liquid ventilation. These gas exchangers, under conditions of 100% oxygen gas ventilation, were eventually replaced by a system of only absorbing carbon dioxide, relying on a pure oxygen inflow. Ultimately, however, it became clear that very small amounts of perfluorocarbon, on the order of 50% of the lung Functional Residual Capacity (FRC, ordinarily about 15 mL/kg), could be used for liquid infusion. This discovery suggested that the gas exchanger and CO2 absorption system might not be needed, and ultimately lead to the use of a much simpler and more effective gas ventilation system described in this patent application.

Overall, the foregoing limitations of the Prior Device resulted in a device that was not sufficiently reliable and portable to be used by paramedics or other emergency personnel away from a medical setting with access to highly skilled, licensed physicians and the Prior Device exhibited heat exchange cooling rates that were potentially too slow to be successfully used in an emergency setting.

SUMMARY

An apparatus for the delivery and removal of a biocompatible liquid to and from the lungs of a mammal is disclosed, with the apparatus comprising an ice water container having an open top end and adapted for containing ice water; a biocompatible liquid tank having an open top end with said biocompatible liquid tank disposed within the ice water container and adapted for containing a biocompatible liquid; a biocompatible liquid infusion reservoir having an open top end with said biocompatible liquid infusion reservoir disposed within the biocompatible liquid tank; a heat exchanger, ice water pump and sprayer disposed within the ice water container, with the ice water pump and sprayer having a tubular connection to the heat exchanger; an electrically operated refill pump disposed within the biocompatible liquid tank, with the pump having a tubular connection with the infusion reservoir; an electrically operated return pump and a return tube disposed within the biocompatible liquid tank, with the return pump and return tube having a tubular connection with the heat exchanger; a pump assembly platform, adapted for placement upon the open top end of the biocompatible liquid tank, said platform containing an electrically operated infusion pump adapted for tubular connection to a sidewall of the infusion reservoir, an electrically operated ice water pump adapted for tubular connection to an ice water supply assembly disposed within the ice water container, and an electrically operated suction pump adapted for tubular connection to a sidewall of the biocompatible liquid tank; a insulation jacket assembly having a watertight open passage within the jacket assembly; and a tube assembly comprising a biocompatible liquid infusion tube, a biocompatible liquid suction tube, an ice water supply tube, and an ice water return tube, said infusion tube partially disposed within the passage within the insulation jacket with an open end of tube extending through a first end of the jacket and adapted for a tubular connection to the infusion pump and with the other open end of the tube extending through a second end of the jacket and adapted for tubular connection to an endotracheal tube, said suction tube adapted at an open end for tubular connection to the suction pump and at the other open end to the endotracheal tube, said ice water supply tube partially disposed within the passage within the insulation jacket with an open end of the tube extending through the first end of the jacket and adapted for tubular connection to the ice water pump and with the other open end disposed within the passage within the jacket, and said ice water return tube adapted at an open end for tubular connection to the passage within the insulation jacket and positioned at the other open end for retuning ice water to the ice water container; and said tube assembly further comprising an air bag adapted for tubular connection to an oxygen supply source and to the endotracheal tube.

Also disclosed is a method of heat exchange in the lungs of a mammal, comprising the steps of cooling a first volume of biocompatible liquid; collecting a second volume of biocompatible liquid from the first volume of cooled biocompatible liquid with said second volume based upon the weight of the mammal; starting the continuous delivery of the second volume of the biocompatible liquid to the lungs of the mammal; supplying a breath of air to the lungs of the mammal manually while delivering the second volume of biocompatible liquid to the lungs; terminating the delivery of the second volume of biocompatible liquid to the lungs of the mammal within 3.5 seconds after starting the delivery of said liquid; starting the continuous removal of the second volume of the biocompatible liquid from the lungs of the mammal as soon as the delivery of the liquid has been terminated; and terminating the removal of the second volume of biocompatible liquid to the lungs of the mammal within 4.5 seconds after starting the removal of said liquid.

BRIEF DESCRIPTION OF THE DRAWINGS

FIG. 10A is an illustration of the tube assembly.

FIG. 10B is an end view of the tube assembly as in FIG. 10A, showing cross section line A-A

FIG. 18 is a graph illustrating the results of using the portable heat exchange apparatus to administer heat exchange within the lungs of four canines.

DETAILED DESCRIPTION OF PREFERRED EMBODIMENTS

Figure 1:
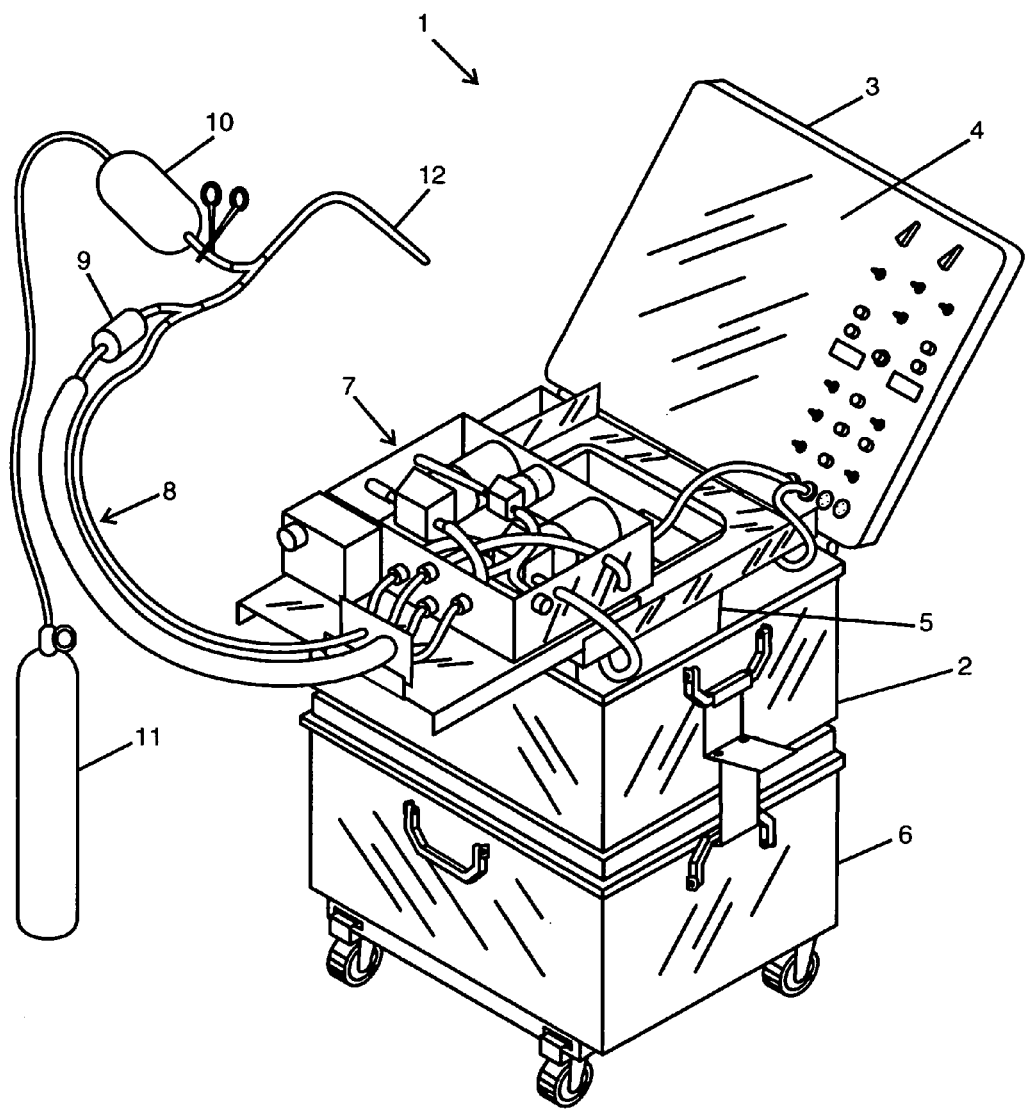
FIG. 1 is a front perspective view of a portable heat exchange apparatus for the delivery and removal of an oxygenated biocompatible liquid to and from the lungs of a patient.

FIG. 1 is an illustration of a portable heat exchange apparatus 1 in its fully assembled condition for the delivery and removal of a biocompatible liquid, such as a perfluorocarbon, to and from the lungs of a human patient or other mammal. In general, the portable heat exchange apparatus 1 contains an ice water container 2 having a hinged lid 3, with an electrical control panel 4 disposed on the inside surface of lid 3. Ice water container 2 is releasably attached to a storage container 6 that is disposed underneath ice water container 2. When lid 4 is opened, a pump assembly 7 can be disposed over the open top end of ice water container 2, and as will be described in more detail in connection with FIG. 11, pump assembly 7 is connected to ice water container 2, to biocompatible liquid tank 5, and to a tube assembly 8 that also includes endotracheal tube 12, filter 9, air bag 10 which is adapted for connection to oxygen supply tank 11.

Figure 2:
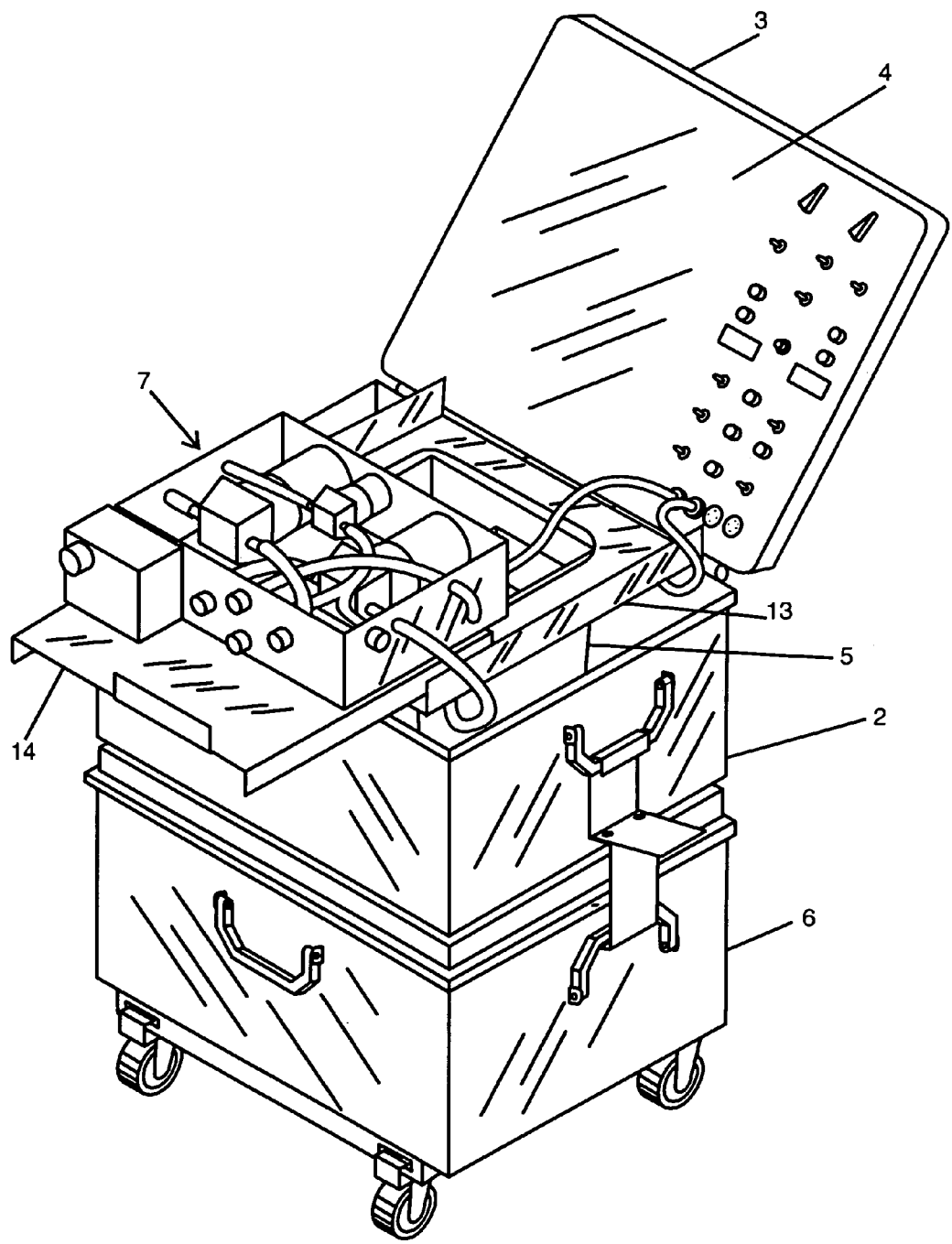
FIG. 2 is a front perspective view as in FIG. 1 with a tube assembly disconnected from a pump assembly.
Figure 3A:
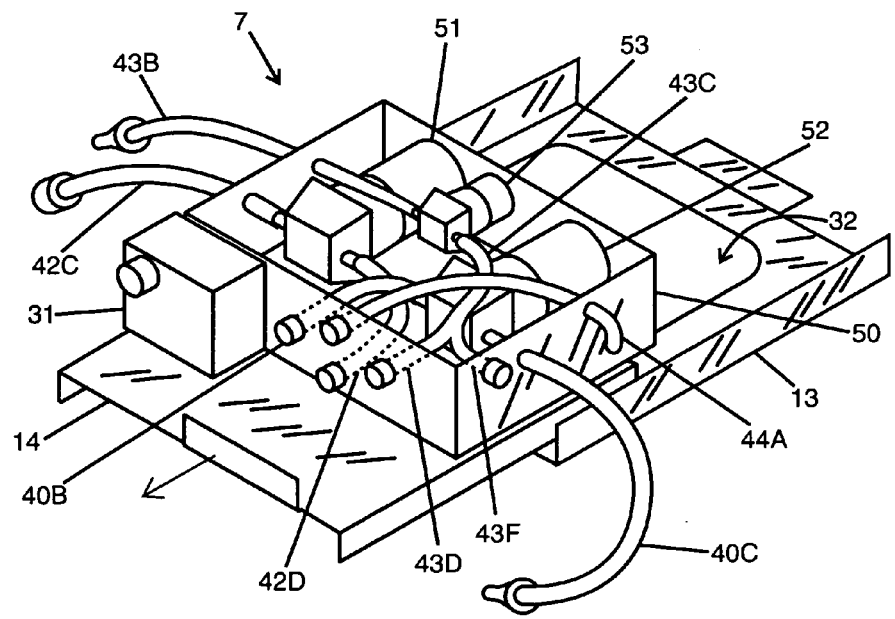
FIG. 3A is a front perspective view of the pump assembly as in FIG. 2 with the pump assembly removed from the portable heat exchange apparatus and showing in more detail a pump tray slidably disposed in an open position.
Figure 3B:
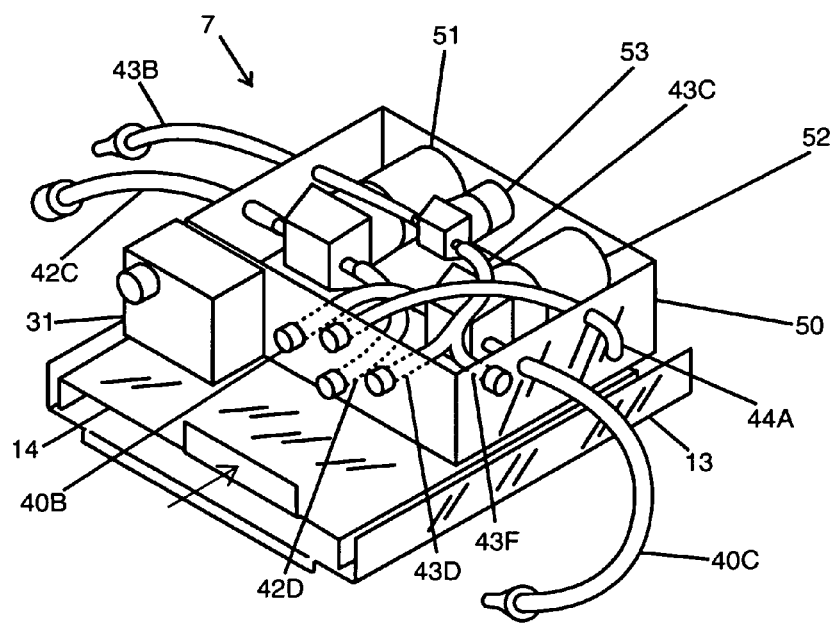
FIG. 3B is a front perspective view of the pump assembly as in FIG. 3A with the pump tray slideably disposed in a closed position.

FIG. 2 is an illustration of portable heat exchange apparatus 1 in a partially disassembled condition with tube assembly 8 removed from the apparatus, and more clearly shows that pump assembly 7 also consists of a pump platform 13 and a pump tray 14, with pump tray 14 slideably disposed towards the front of apparatus 1, relative to pump platform 13 and to ice water container 2. FIGS. 3A and 3B are isolated illustrations of pump assembly 7, showing that assembly 7 can be completely removed from portable heat exchange apparatus 1, and further demonstrating that pump tray 14 can be slideably disposed relative to pump platform 13, so as to uncover an opening 32 within pump platform 13. When pump platform 13 is positioned over the open top end of ice water container 2, opening 32 provides access to biocompatible liquid tank 5.

Figure 4:
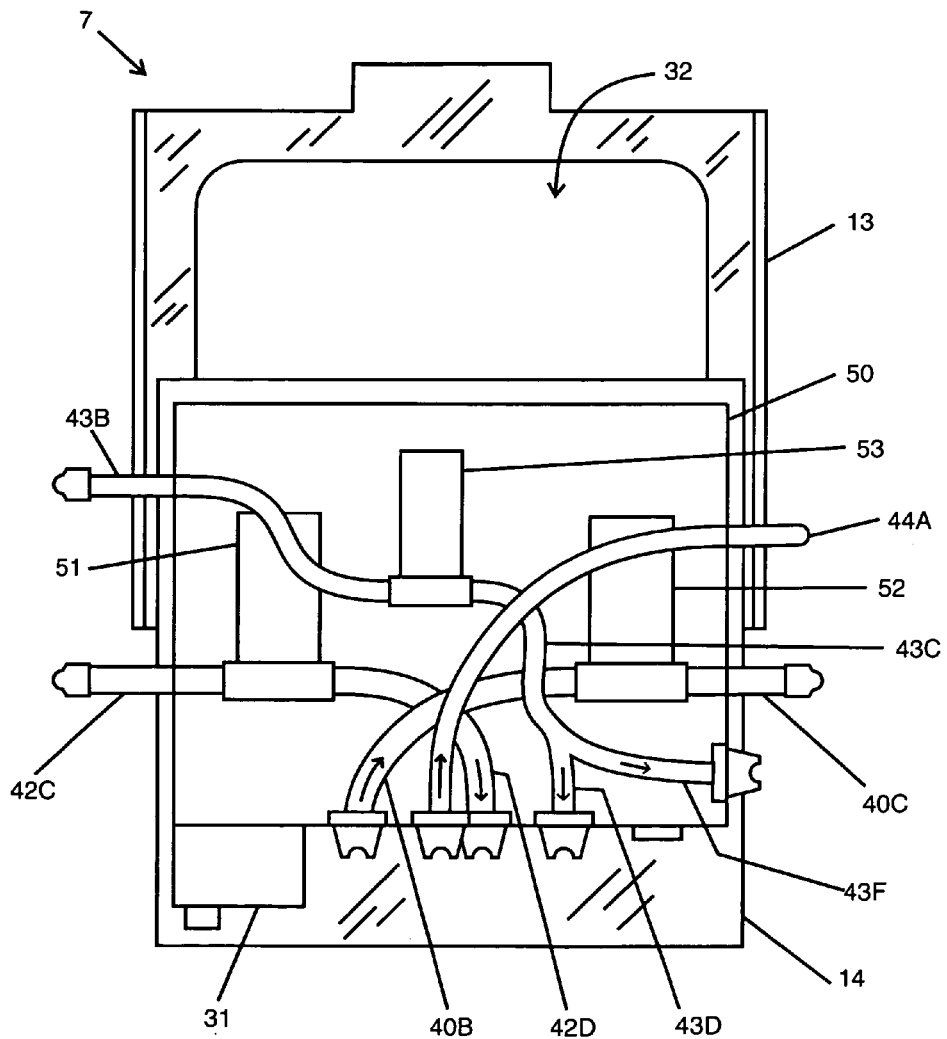
FIG. 4 is a top plan view of the pump assembly as in FIGS. 2 and 3A.

Referring to FIGS. 3A, 3B and 4, pump assembly 7 includes an electrically operated biocompatible liquid infusion pump and suction pump, 51 and 52, respectively, and an electrically operated ice water jacket pump 53 that are all disposed within a pump housing 50 that is attached to pump tray 14. A biocompatible liquid infusion tube 42C extends through an opening in pump housing 50, with an open end of the tube attached to infusion pump 51 with the other open end having a quick release male fitting, and another infusion tube 42D is attached at an open end to the opposite side of infusion pump 51, with the other open end of the tube having a quick release female fitting that is disposed within pump housing 50. A suction tube 40B is attached at an open end to suction pump 52 with the other open end of the tube connected to a quick release female fitting that is disposed within pump housing 50, and a second suction tube 40C extends through an opening in pump housing 50, with an open end of the tube attached to the opposite side of suction pump 52 and with the other open end of the tube connected to a quick release male fitting. An ice water supply tube 43B extends through an opening in pump housing 50, with an open end of the tube attached to ice water jacket pump 53 with the other open end having a quick release male fitting, and with another supply tube 43C, having two separate tube branches, 43D and 43F, attached to the opposite side of ice water jacket pump 53. The terminal open ends of tube branches 43D and 43F are each connected to quick release female fittings that are disposed within pump housing 50. An ice water return tube 44A extends through an opening in pump housing 50, with an open end of the tube connected to a quick release female fitting that is disposed within pump housing 50 and with the other open end of the tube extending away from pump housing 50 forming an elbow. A pump speed controller 31 is connected to outside surface of pump housing 50 and is in electrical connection with infusion pump 51.

Figure 5:
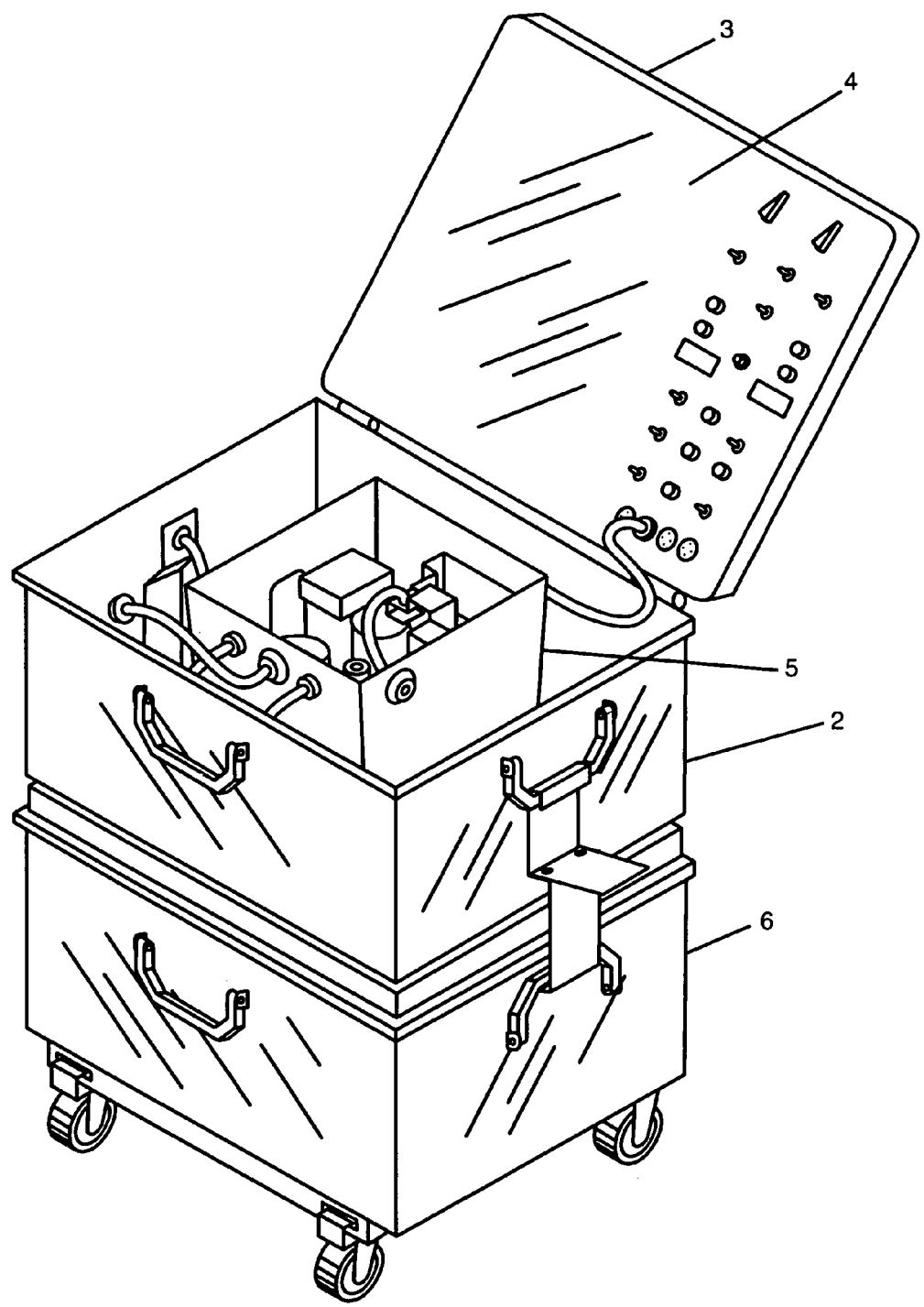
FIG. 5 is a front perspective isolated view as in FIG. 2 with the pump assembly removed from the portable heat exchange apparatus, illustrating a biocompatible liquid tank disposed within an ice water container.
Figure 6A:
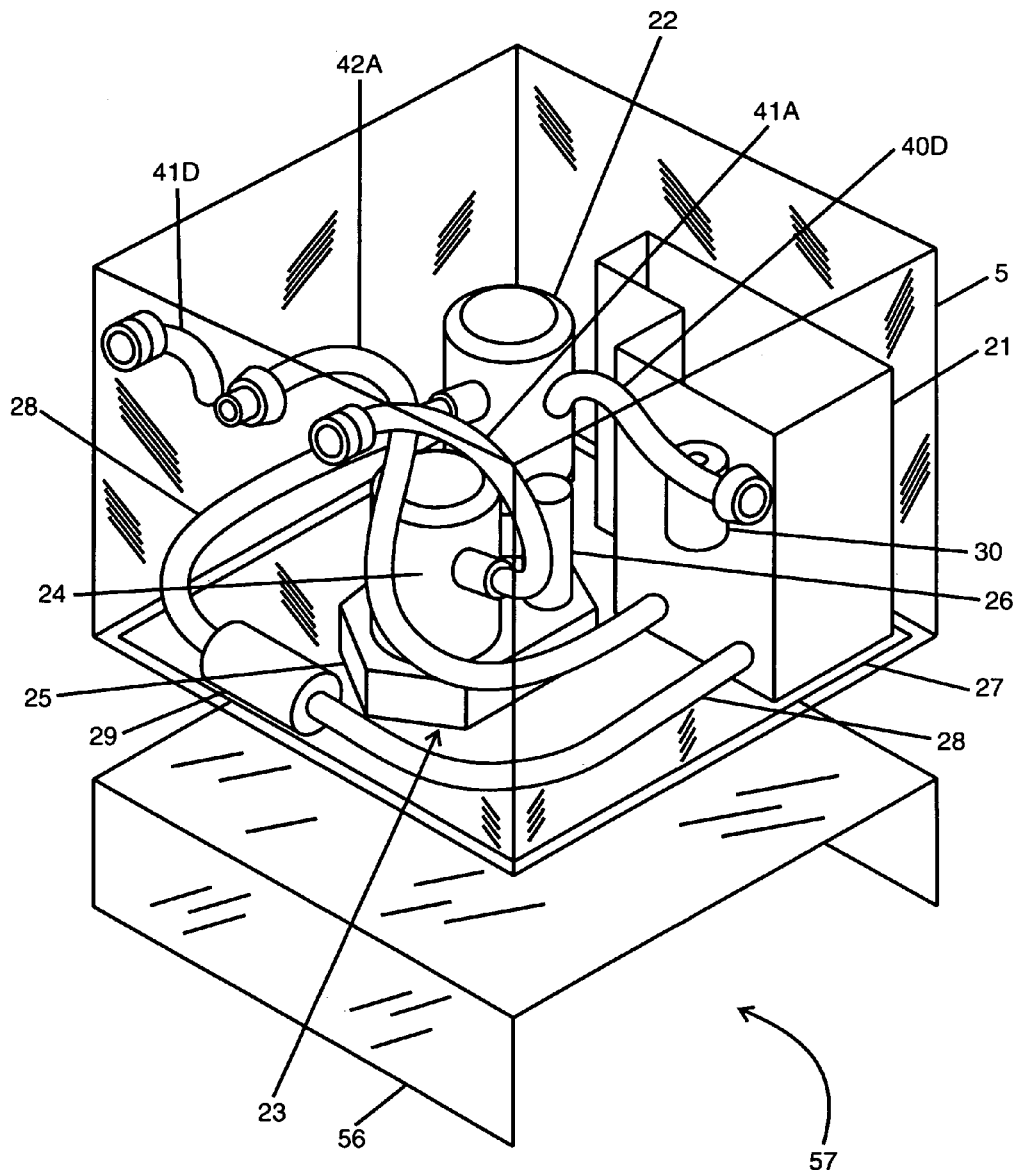
FIG. 6A is an isolated view of the biocompatible liquid tank as in FIG. 5, further illustrating a biocompatible liquid reservoir disposed within the biocompatible liquid tank.
Figure 6B:
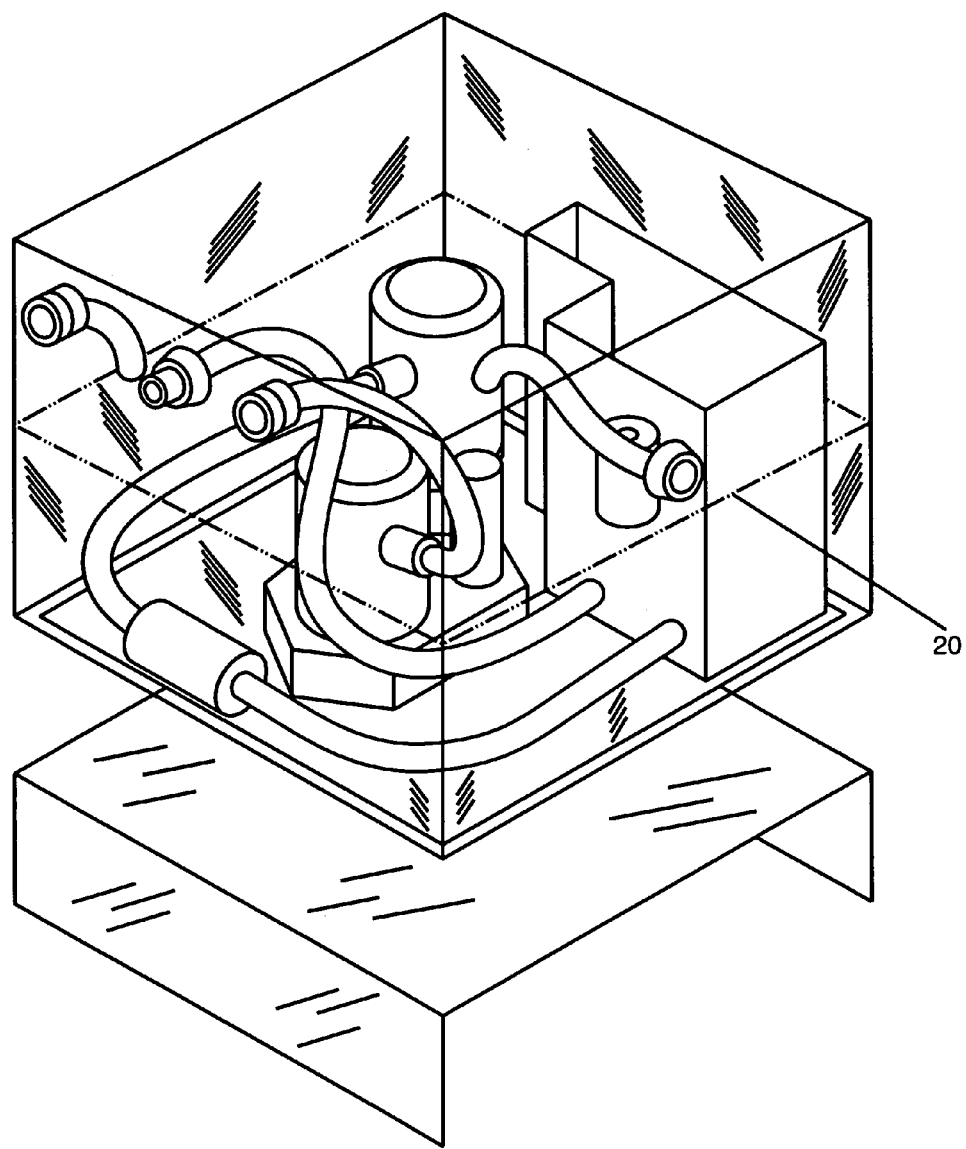
FIG. 6B is the isolated view of the biocompatible liquid tank as in FIG. 6B further illustrating a level of biocompatible liquid in the tank.

FIG. 5 illustrates the portable heat exchange apparatus 1 with the pump assembly 7 removed so as to show the biocompatible liquid tank 5 disposed within the ice water container 2, and in order to further illustrate tank 5, it is shown in an isolated view in FIGS. 6A and 6B. Biocompatible liquid tank 5 has four vertical sidewalls, a bottom panel and an open top end. The sidewalls are preferably made of clear plastic in order to facilitate observation of the components within tank 5, as well as biocompatible liquid level 20 as shown in FIG. 6B, and the bottom panel is adapted to rest on a box-shaped platform 56. Box-shaped platform 56 has two elongate and opposite sidewalls that are connected at the top of each sidewall to a horizontal top panel and are connected at the bottom of each sidewall to the bottom inside surface of ice water container 2, thereby leaving an open space 57 under platform 56. FIG. 6A illustrates box-shaped platform 56 in an exploded view in order to show its position under biocompatible liquid tank 5. A base plate 27 is removably positioned within tank 5 such that it rests on the inside bottom surface of tank 5. A biocompatible liquid infusion reservoir 21 having six vertical sidewalls, a bottom panel, and an open top end is disposed within biocompatible liquid tank 5, with the bottom panel of reservoir 21 attached to the top surface of base plate 27. An electrically operated refill pump 22 and a pump manifold 23 are both disposed within biocompatible liquid tank 5 and connected to the top surface of base plate 27. Pump manifold 23 includes an electrically operated return pump 24, a base plenum 25, and an inlet pipe 26, having an open top end. A tube 28 is connected at an end to refill pump 22 and at the other end to reservoir 21, and a check valve 29 is inserted within tube 28 between its two ends. An infusion tube 42A is connected at an open end in a watertight manner to an opening through infusion reservoir 21, and at the other open end to a quick release male fitting that is positioned in a watertight manner through an opening in a side wall of tank 5. A tube 41A is connected at an open end to return pump 24 and at the other open end to a threaded connection positioned in a watertight manner through an opening in a sidewall of tank 5. A return tube 41D is connected at an open end to a threaded connection positioned in a watertight manner through an opening in a sidewall of tank 5, and the other open end of the tube is positioned near the top of the sidewall such that it is normally above biocompatible liquid level 20. And, a suction tube 40D is connected at an open end to a quick release male fitting that is positioned in a watertight manner through an opening in a sidewall of tank 5, and the other end of the tube is positioned such that it is normally above the biocompatible liquid level 20 and above the opening in inlet pipe 26. A level sensor 30 is disposed within the biocompatible liquid tank 5 and is attached to an outside surface of a sidewall of reservoir 21. Sensor 30 includes the feature of sounding an electronic alarm when the biocompatible liquid level falls below the level of the sensor. FIG. 6B illustrates the biocompatible liquid level 20 after the liquid has been added to the biocompatible liquid tank 5 as illustrated in FIG. 6A.

Figure 7A:
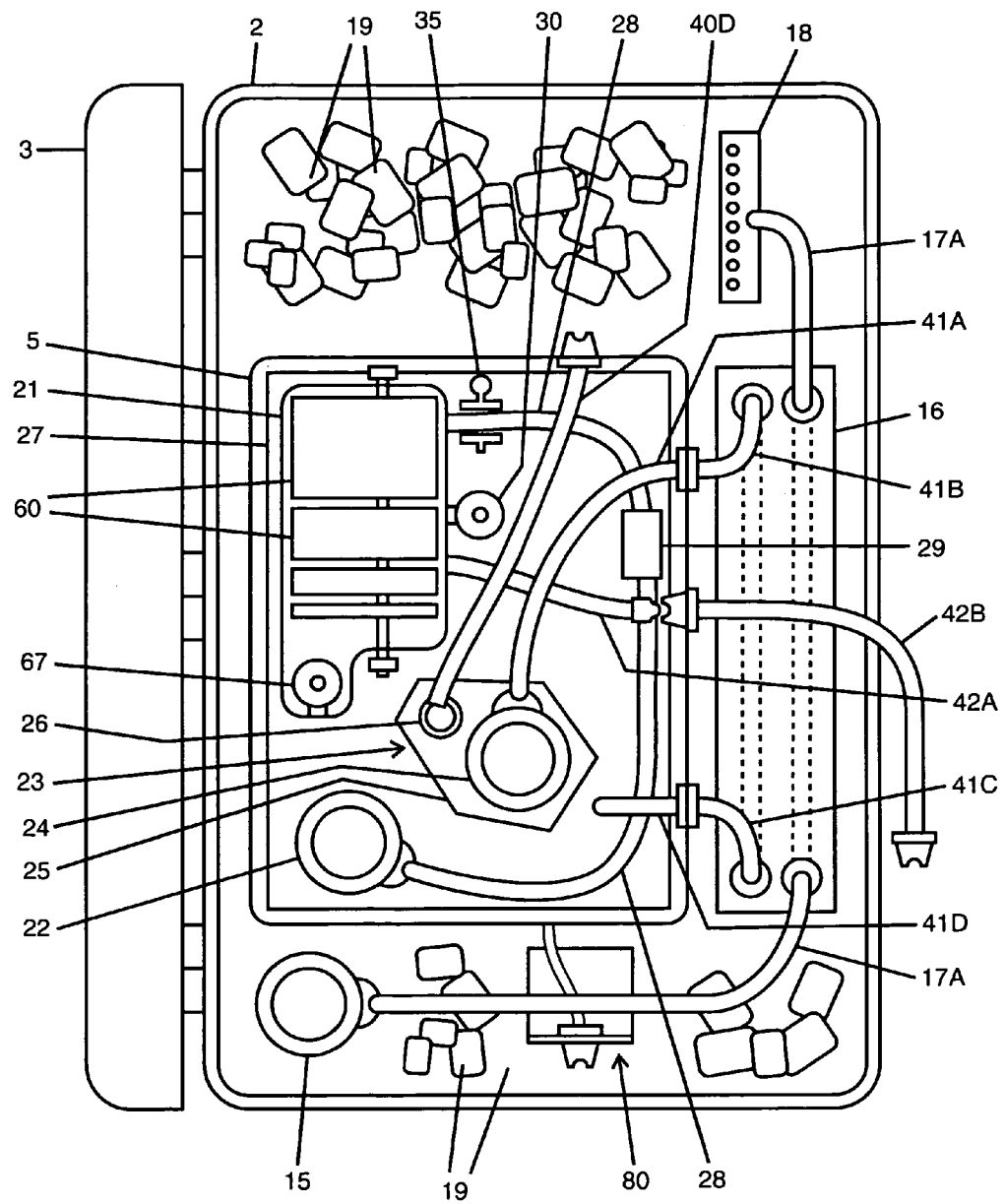
FIG. 7A is a top plan view of the biocompatible liquid reservoir disposed within the biocompatible liquid tank, and with the tank disposed within the ice water container.

FIG. 7A is a top plan view illustration of the ice water container 2, with lid 3 in an upright, open position. The ice water container 2 contains biocompatible liquid tank 5, which contains infusion reservoir 21. The ice water container 2 also contains a heat exchanger 16 and an electrically operated ice water pump 15, which are positioned adjacent to the bottom inside surface of container 2, and a water sprayer 18 that is connected to a sidewall of ice water container 2. Heat exchanger 16 is operably connected to ice water pump 15 and to water sprayer 18. A tube 17A is connected at an open end to ice water pump 15 and is connected at the other open end to an end of heat exchanger 16. A tube 17B is connected at an open end to the opposite end of heat exchanger 16 and is connected at the other open end to water sprayer 18. In operation, the ice water tank 2 is partially filled with ice and water 19. The biocompatible liquid tank 5 and its contents have been previously described in connection with the description of FIGS. 5, 6A and 6B above. Heat exchanger 16 is also operably connected to return pump 24 and to the biocompatible liquid tank 5. As described above, tube 41A is connected at an end to return pump 24 and at the other end to a threaded connection that is disposed in a watertight manner within a sidewall of tank 5. A tube 41B is connected at an end to a threaded connection that is mated to the threaded connection at the end of tube 41A and the other end of tube 41B is connected to an of heat exchanger 16. As also described above, tube 41D is connected at an open end to a threaded connection that is disposed in a watertight manner within a sidewall of tank 5, with the other open end of the tube positioned such it is normally above biocompatible liquid level 20. A tube 41C is connected at an end to the other end of heat exchanger 16, with the other end of the tube connected to a threaded connection that is mated to the threaded connection at the end of tube 41D.

Figure 7B:
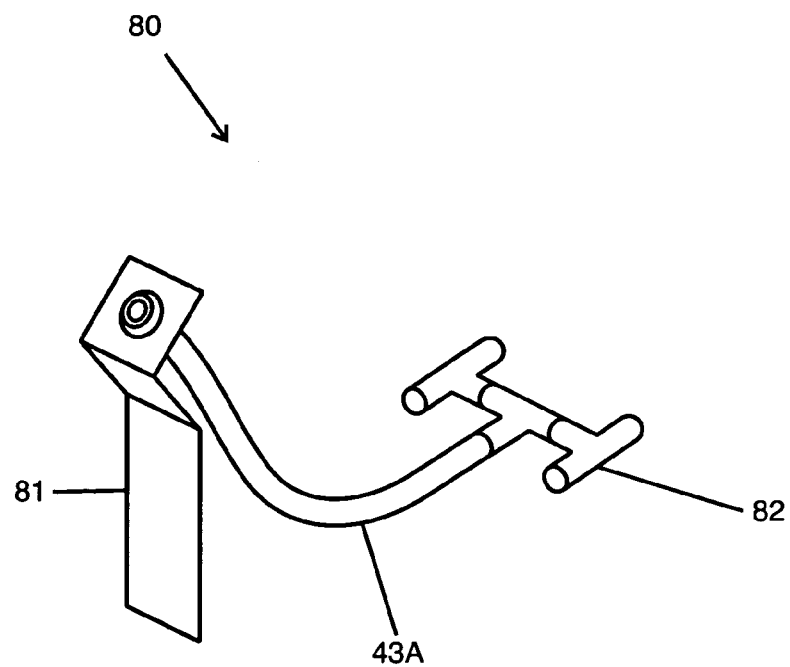
FIG. 7B is a perspective illustration of an ice water delivery assembly.

FIG. 7B illustrates an ice water supply assembly 80 that is also disposed within ice water container 2. An elongate stand member 81 has a top end and a bottom end, with the bottom end resting on the inside, bottom surface of ice water container 2. An ice water supply tube 43A is connected at an open end to a quick release female fitting that is mounted through an opening in the top end of stand member 81 and is connected at the other open end of the tube to an "H" shaped tubular member 82 having two parallel and opposite tubular segments that are open at each end and with the segments connected to a cross tubular segment (forming the "H") where supply tube 43A is attached. Elongate stand member 81 is positioned within ice water container 2 such that "H" shaped tubular member 82 is disposed within open space 57 within box-shaped platform 56, as shown in FIG. 6A.

Figure 8:
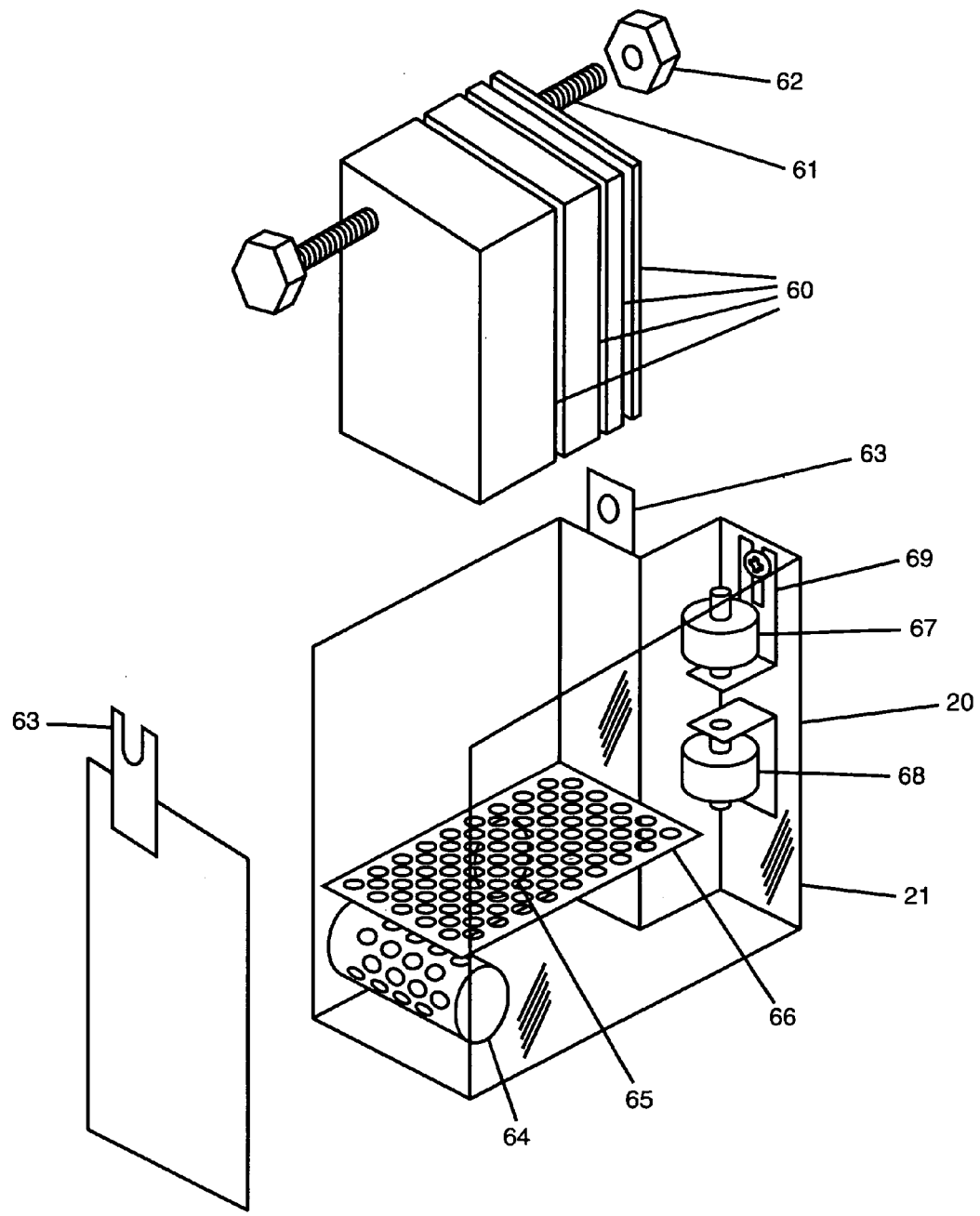
FIG. 8 is a partially exploded perspective view of the biocompatible liquid reservoir.

FIG. 8 presents a more detailed illustration of infusion reservoir 21. As shown in the figure four volume displacement tabs 60 are disposed within reservoir 21 by hanging the tabs on a bolt 61 secured by nut 62. Although four displacement tabs 60 are illustrated in the figure, any lesser number of displacement tabs could be used. Bolt 61 is passed through an opening within a first flange of bolt mount 63 and rests in a cradle within a second flange of bolt mount 63. In operation, the biocompatible liquid enters the reservoir 21 though tube 28 that is connected to a watertight opening through a side wall of reservoir 21 and enters a cylindrically shaped biocompatible liquid inlet 64 that is disposed near the bottom of reservoir 21. Inlet 64 has a closed end and a plurality of openings through its cylindrical wall that causes the biocompatible liquid to more evenly disperse as it enters reservoir 21. The biocompatible liquid exits from reservoir 21 through an outlet 65, consisting of an opening through a sidewall of reservoir 21 and a watertight connection to infusion tube 42A. A diffusion baffle 66 is disposed within reservoir 21 just above inlet 64 and outlet 65 and is generally parallel to the bottom of reservoir 21. Baffle 66 acts to further disperse the biocompatible liquid as it enters and exits reservoir 21, thus serving to minimize surges of liquid that would interfere with precise measurement of liquid volume in reservoir 21. A high-level float sensor 67 is connected to a level adjustment assembly 69 that is attached to an inside surface of a sidewall of reservoir 21, and a low-level float sensor 68 is disposed below high-level float sensor 67 and is attached to an inside surface of a sidewall of reservoir 21. High-level sensor 67 is electrically connected with refill pump 22 in such a way that it interrupts power to refill pump 22 when the liquid level in reservoir 21 has reached its maximum desired level. The low-level sensor is electrically connected with infusion pump 51 in such a way that it interrupts power to infusion pump 51 when the liquid level in reservoir 21 has diminished to its minimum desired level. Adjustment assembly 69 includes an adjustment screw that allows high-level float sensor 67 to be positioned higher or lower relative to the level of the biocompatible liquid 20 in reservoir 21.

Figure 9:
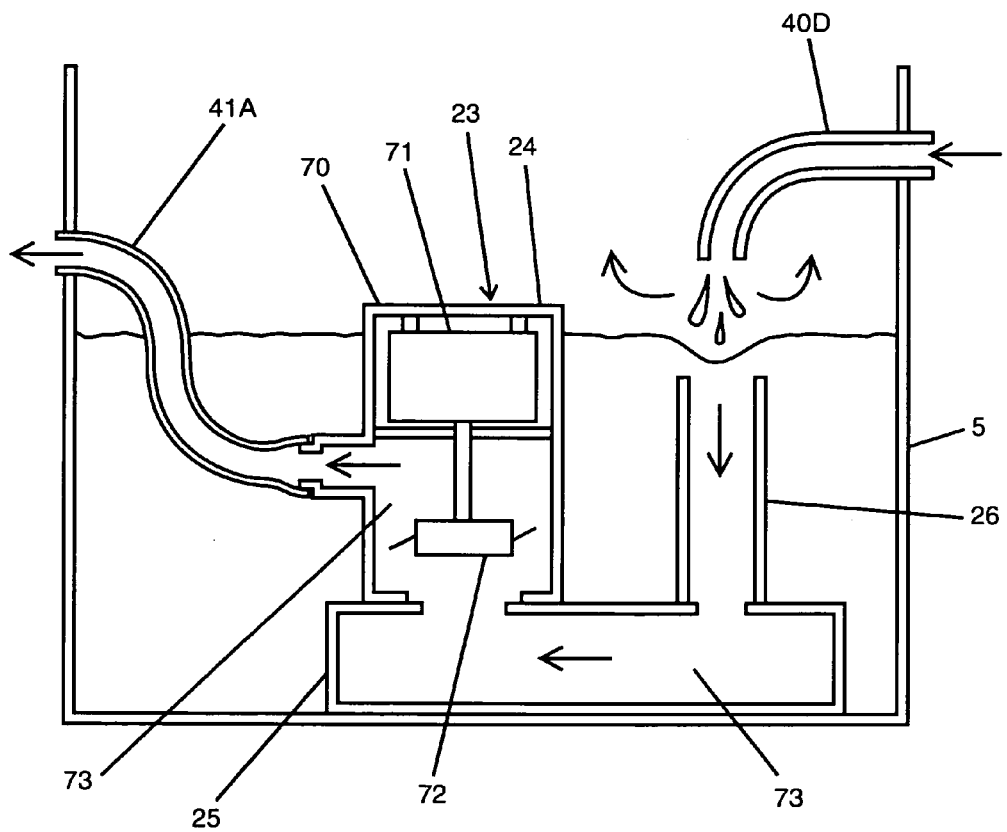
FIG. 9 is a schematic illustration of the flow of a biocompatible liquid through a pump manifold within the biocompatible liquid tank.

FIG. 9 sets forth a more detailed illustration of pump manifold 23, which comprises a pump plenum 25 that is disposed on the bottom inside surface of tank 5 with plenum 25 having an open chamber 73. A vertical pipe 26 is in tubular connection at a bottom end to plenum 25 and impeller chamber 73 and a top open end of the pipe is positioned such that it is generally below the open end of suction tube 40D. Pump 24 has an impeller 72 that is disposed within chamber 73, with the impeller in operable connection to an electrical pump motor 71 that is disposed within a watertight pump housing 70, positioned above and adjacent to plenum 25. In operation the warmed biocompatible liquid returning from the lungs of a patient enters biocompatible liquid tank 5 through the open end of suction tube 40D, which is above level 20 of the biocompatible liquid in tank 5. As the warm biocompatible liquid cascades into tank 5, almost all of the returning air, which has been mixed in the liquid while in the lungs of the patient, disperses to atmosphere, and the warm biocompatible liquid enters pump manifold 24 by generally flowing into the open end of tube 26. The spinning pump impeller 72 reduces the liquid pressure inside of impeller chamber 73, which in turns causes the biocompatible liquid to start flowing through impeller chamber 73 (in the direction of the arrows in FIG. 9) and then exiting through an opening through chamber 73 that is connected to tube 41A that returns the liquid to heat exchanger 16. The spinning impeller 72 also creates a vortex effect at the open end of inlet pipe 26, which in turn causes more of the cascading biocompatible liquid to enter impeller chamber 73. As a result, pump manifold 23 provides for a more efficient cooling of the warm biocompatible liquid returning from the patient, because most of the warmed liquid is returned directly to heat exchanger 16 for cooling, rather than first mixing with the other cooler biocompatible liquid in tank 5 that has already been cooled by heat exchanger 16.

Figure 10C:
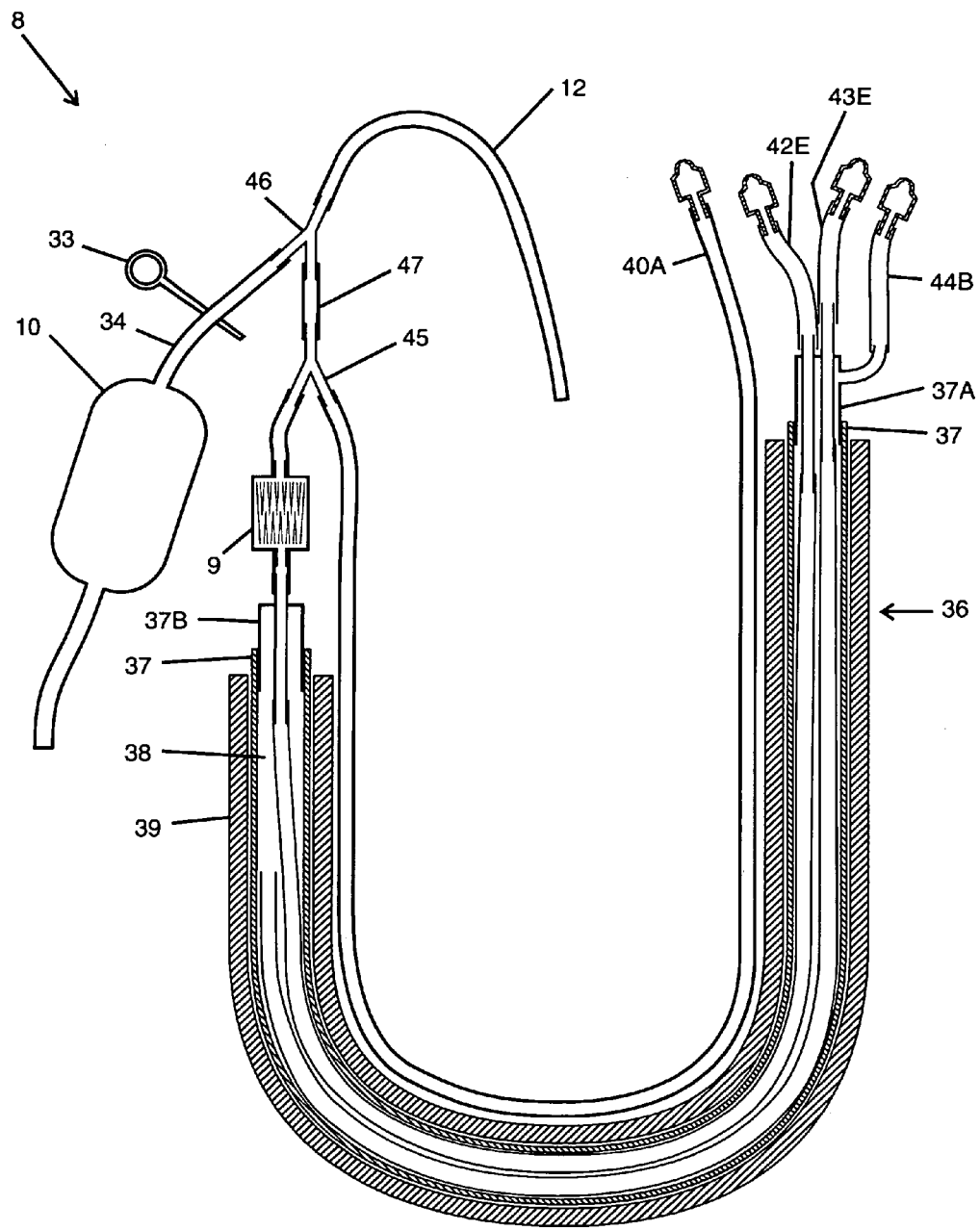
FIG. 10C is a cross sectional view of the tube assembly as in FIG. 10A and 10B, taken along section line A-A.

FIGS. 10A, 10B and 10C illustrate in more detail tube assembly 8. Referring primarily to the cross-sectional view in FIG. 10C, an insulation jacket assembly 36 comprises a tube 37, connected in a watertight manner at an end to end cap 37A and at the other end to end cap 37B, thereby forming a watertight tubular open space or passage 38. Insulation jacket assembly 36 also comprises a cylindrically shaped batt of insulation 39 that envelops tube 37. Infusion tube 42E is disposed within open space 38 with an open end of the tube extending in watertight manner through end cap 37A and connecting to a quick release male fitting, and with the other open end of the tube extending in a watertight manner through end cap 37B and connecting to an end of filter 9. Supply tube 43E is also disposed within open space 38 with an open end of the tube extending in a watertight manner through end cap 37A and connecting to a quick release male fitting, and with the other open end of the tube disposed within open space 38. Return tube 44B is connected at an open end to end cap 37A and is connected at the other end to a quick release male fitting. Suction tube 40D is connected at an open end to a quick release male fitting and the other end to a first branch of a first tubular "Y" fitting 45. A second branch of first tubular "Y" fitting 45 is connected with a short tube to filter 9, and a third branch of "Y" fitting 45 is connected with a short tube to the first branch of a second tubular "Y" fitting 46. Endotracheal tube 12 is connected to a second branch of tubular "Y" fitting 46. An end of air bag 10 is connected by means of a tube to a third branch of the second tubular "Y" fitting 46, and the other end is adapted for connection to oxygen supply tank 11.

Figure 11:
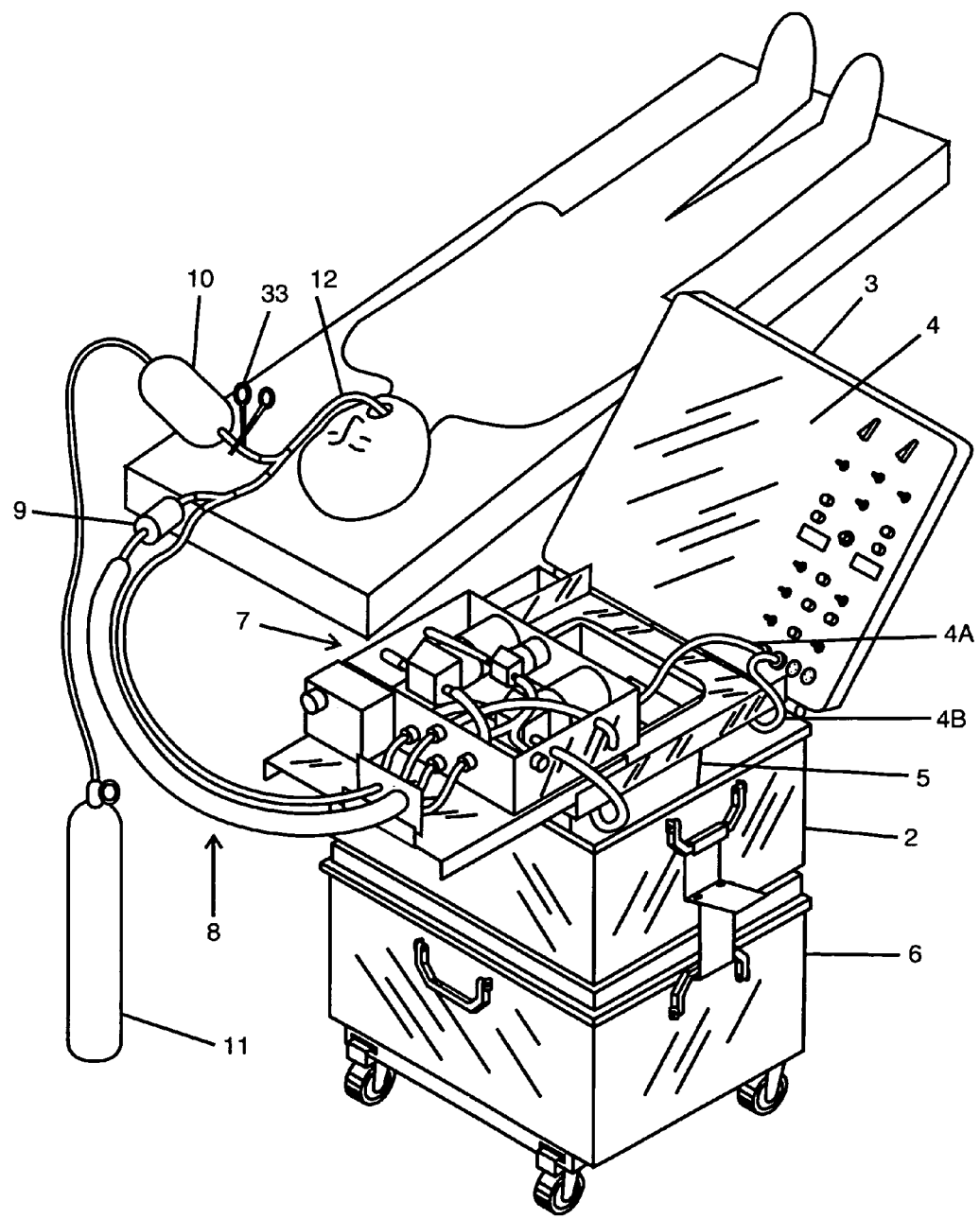
FIG. 11 is an illustration of the portable heat exchange apparatus as in FIG. 1 that is connected to a patient for the delivery and removal of an oxygenated biocompatible liquid to and from the lungs of the patient.
Figure 12:
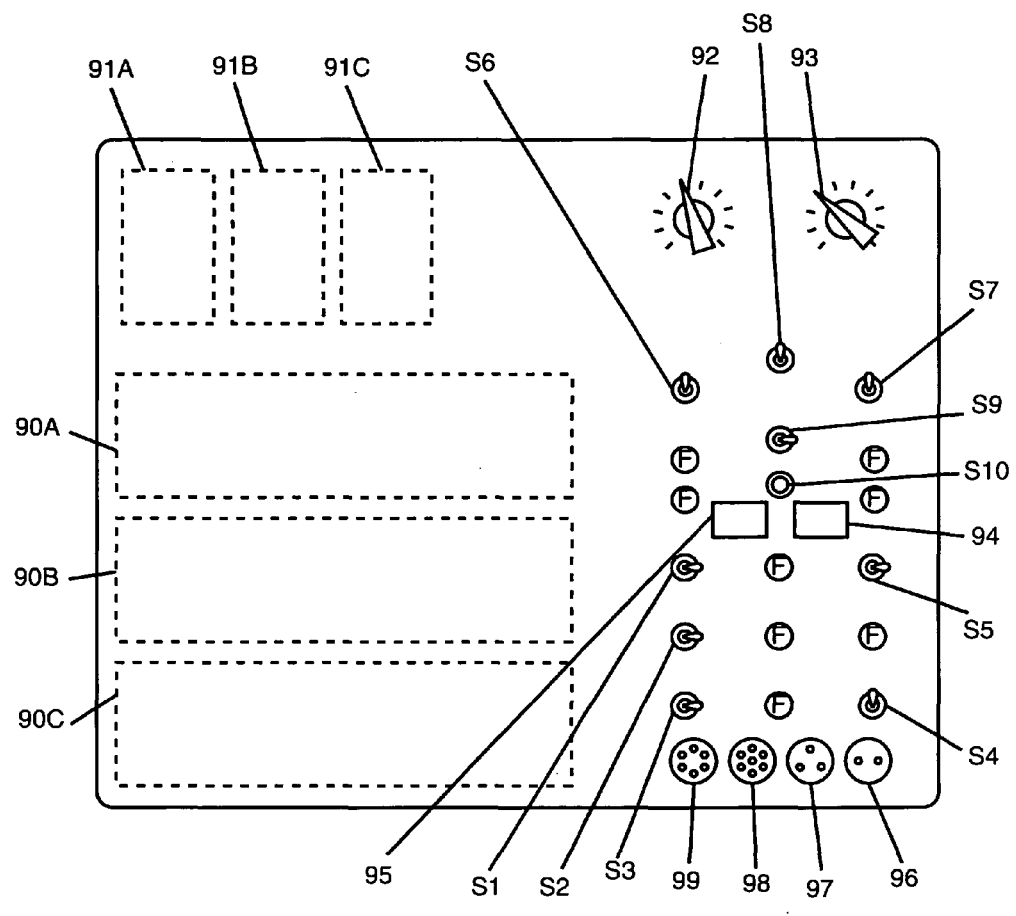
FIG. 12 is an illustration of a control panel.

FIG. 11 illustrates portable heat exchange apparatus 1 in its fully assembled condition with endotracheal tube 12 inserted into the lungs of a patient. Portable heat exchange apparatus 1 is assembled by carrying out the following steps: Infusion reservoir 21 is releasably connected to infusion pump 51 by first connecting an end of an infusion tube 42B, having a quick release female fitting, to the quick release male fitting at the end of infusion tube 42A and releasably connecting the other end of infusion tube 42B, also having a quick release female fitting, to the quick release male fitting at the end of infusion tube 42C. The biocompatible liquid tank 5 is releasably connected to suction pump 52 by connecting the quick release female fitting at the end of suction tube 40D to the quick release male fitting at the end of suction tube 40C. Next, ice water container 2 is releasably connected to ice water jacket pump 53 by connecting a quick release female fitting at the end of supply tube 43A to the quick release male fitting at the end of supply tube 43B. Then, tube assembly 8 is releasably connected to each of the pumps within pump assembly 7. Quick release male fitting at the end of infusion tube 42E is releasably connected to the quick release female fitting at the end of infusion 42D, quick release male fitting at the end of tube supply tube 43E is releasably connected to the quick release female fitting at the end of supply tube 43D, quick release male fitting at the end of return tube 44B is releasably connected to the quick release female fitting at the end of return tube 44A, and the quick release male fitting at the end of suction tube 40A is releasably connected to the quick release female fitting at the end of suction tube 40B. Clamp 33 is attached to tube 34, and electrical wiring connection 4A is plugged into a socket 99 (as shown in FIG. 12) within control panel 4 in order to supply power to pump assembly 7, and connection 4B is plugged into another socket 98 (as also shown in FIG. 12) with in control panel 4 in order to supply power to the pumps and level sensors within ice water container 2, biocompatible liquid tank 5 and infusion reservoir 21. Finally, endotracheal tube 12 is inserted into the lungs of a patient.

Figure 13:
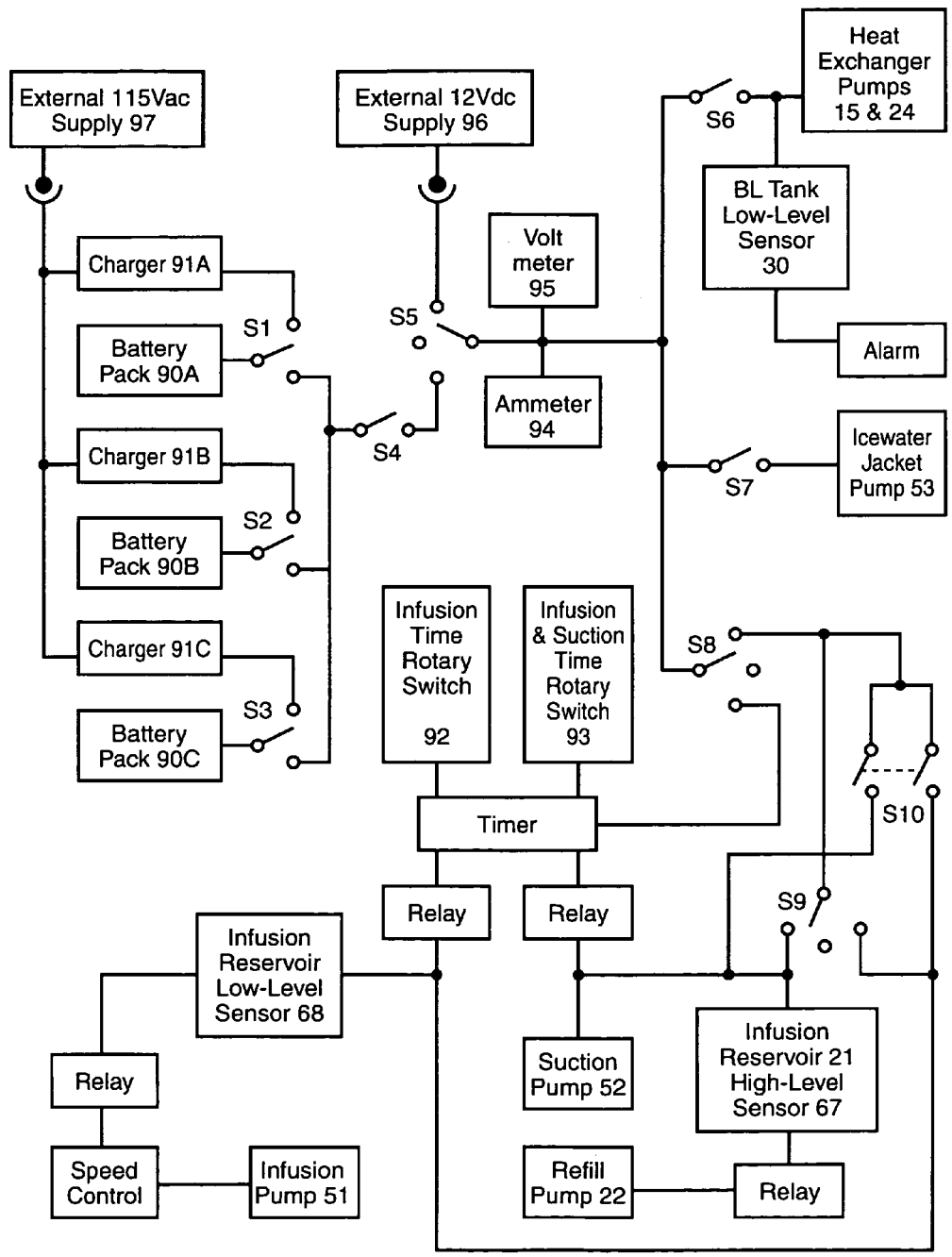
FIG. 13 is a block diagram of an electrical circuit.

All of the above-described electrical components are electronically controlled by means of control switches on control panel 4 that are in operable connection to an electronic circuit and to either an external 12 volt direct current source or to an external 115 volt alternating current source. FIG. 12 illustrates the various control panel switches and the schematic diagram presented in FIG. 13 illustrates the electrical circuit. Referring to both FIG. 12 and FIG. 13, battery packs 90A, 90B, and 90C and battery chargers 91A, 91B, and 91C are disposed behind control panel 4 and within lid 3 of ice water container 2. Control panel 4 contains several toggle switches as follows: toggle switches S1, S2, and S3 control the supply of power to and from battery packs 90A, 90B, and 90C, respectively; toggle switch S4 is a safety disconnect switch for the battery packs; toggle switch S5 allows for the selection of either the external direct current source or the internal battery pack power source; toggle switch S6 is an on-off switch for ice water pump 14 and return pump 24 (referred to as the "heat exchanger pumps"); toggle switch S7 is an on-off switch for ice water jacket pump 53; toggle switch S8 allows for the selection of either a manual or an automatic mode of operation; toggle switch S9 allows for the manual operation of either infusion pump 51 or suction pump 52; and switch S10 is a pushbutton, momentarily activated switch for priming and pre-cooling the biocompatible liquid before endotracheal tube 12 is connected to the patient as in FIG. 11. Selector dial 92 allows for the selection of an infusion cycle time, and selector dial 93 allows for the selection of a total infusion plus suction time. Ammeter 94 and voltmeter 95 are digital displays of the operating current and voltage, respectively. Input sockets 96 and 97 are for external 12 volt direct current source or to an external 115 volt alternating current source, respectively. Output socket 98 is for power output to the pumps and sensors within the ice water container 2, biocompatible liquid tank 5 and reservoir 21, and output socket 99 is for power to the pumps within pump assembly 7.

Figure 14:
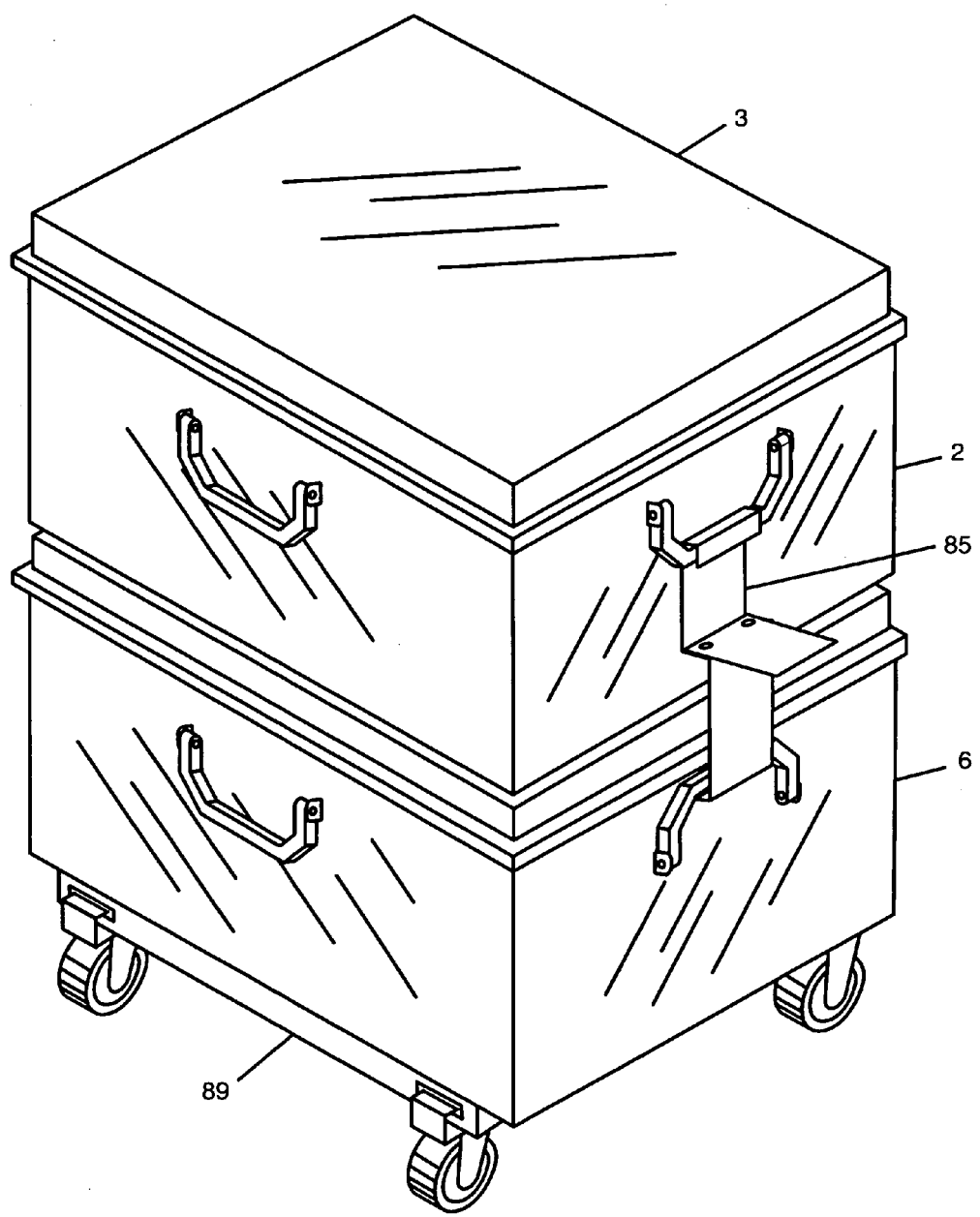
FIG. 14 is a front perspective view of the portable heat exchange apparatus with a lid of the ice container in a closed position and the ice water container disposed above and connected to a storage container by means of a clamp assembly.
Figure 15A:
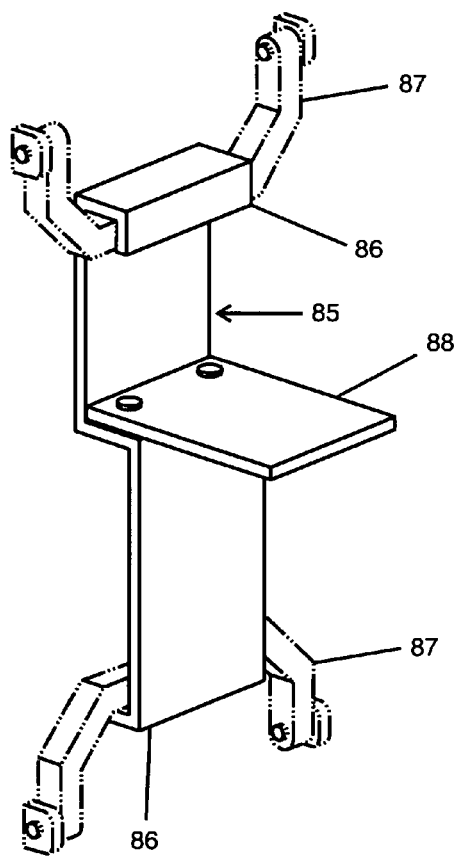
FIGS. 15A and 15B represent a more detailed illustration of the clamp assembly permitting the attachment and release of the ice water container to and from the storage container.
Figure 15B:
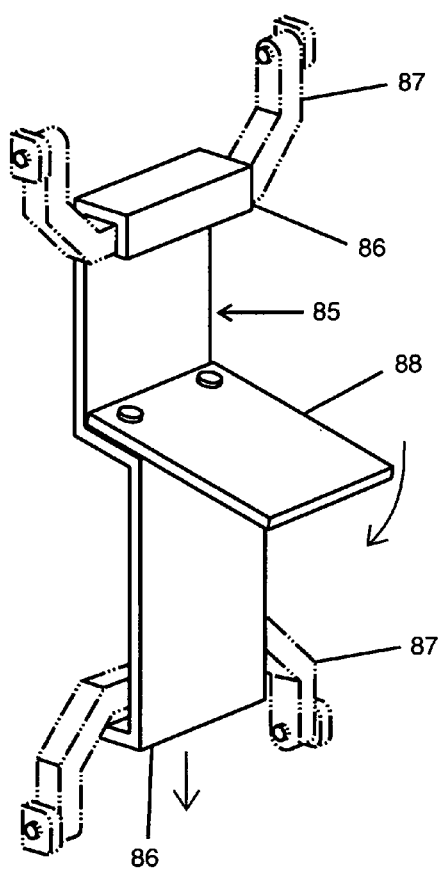

FIG. 14 illustrates portable heat exchange apparatus 1 in a transportable configuration, comprising two similarly sized containers that have been fastened together. Ice water container 2 is positioned on top of storage container 6 and the two containers are fastened together by using a pair of clamp assemblies 85, with one assembly for each side of ice water container 2 and storage container 6. The clamp assemblies 85 fasten ice water container 2 and storage container 6 together by utilizing a hooked member 86 at the end of each assembly, with the hooked member clasping rotatable side handles 87 on each container. As shown in FIGS. 15A and 15B, each clamp assembly 85 can be released by pressing down on flange 88, which in turn extends each clamp hooked member 86 in a downward direction, thereby permitting the removal of each clamp assembly from its respective handles and the separation of the containers. Clamp assemblies 85 are used to fasten the containers together by simply reversing the process of releasing clamp assemblies 85. Connected to the bottom of storage container 6 is a removable frame 89 with four wheels that permit the containers to be transported by rolling them along the ground.

Figure 16:
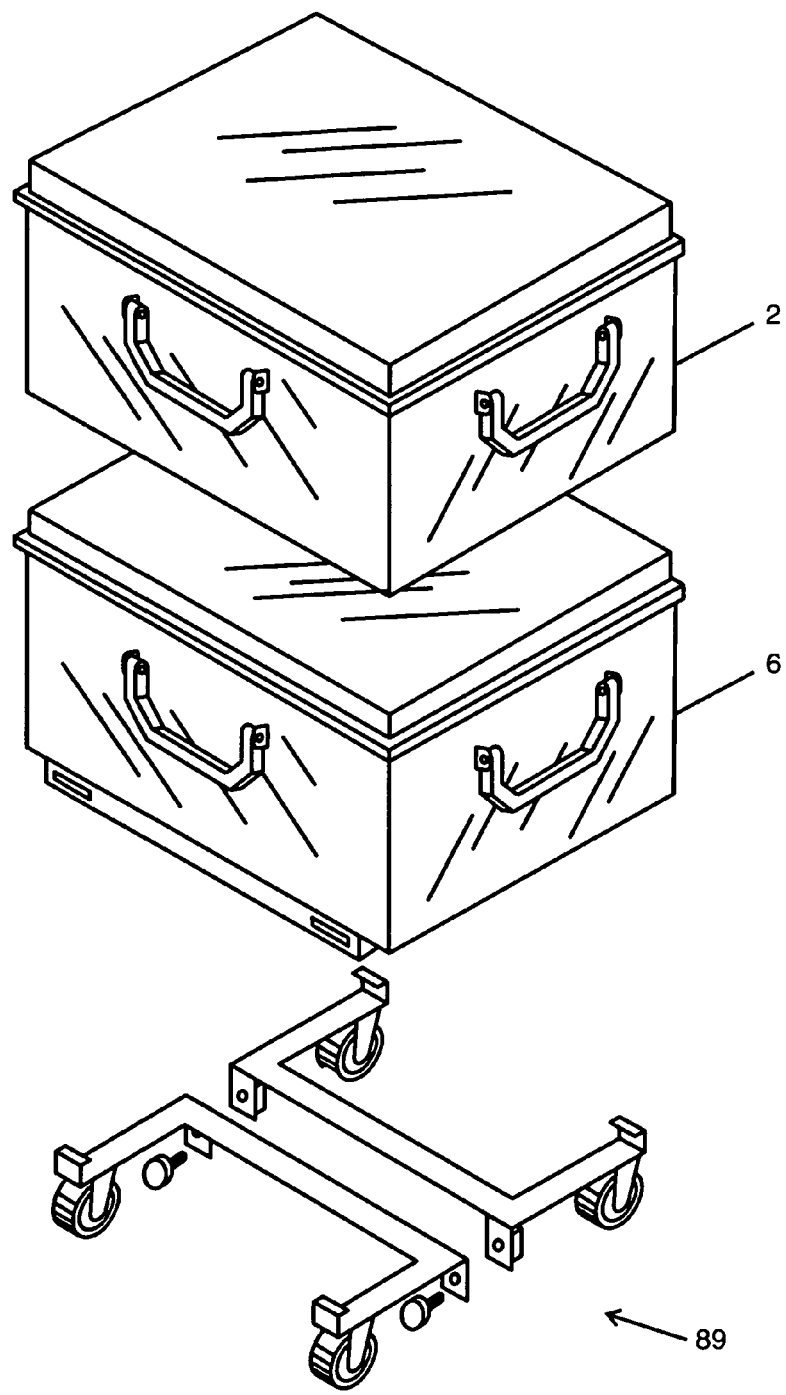
FIG. 16 is an exploded view of the of the portable apparatus as in FIG. 14, illustrating the orientation of the ice water container, storage container, and a bottom frame with wheels.

FIG. 16 illustrates ice water container 2 and storage container 6 after they have been disconnected and further shows removable frame 89 after it has been removed from storage container 6 and disassembled into two frame segments. Disassembly of frame 89 permits it to be stored in storage container 6 by opening its hinged lid and placing the frame inside. Similarly, all of the pumps and tubes that deliver and return the biocompatible liquid to and from the patient can be stored in storage container 6. This is accomplished by disconnecting each of the quick release fittings, removing pump assembly 7 from the top of ice water container 2, and then placing pump assembly 7 and tube assembly 8 inside of storage container 6.

Preferably, ice water container 2 and storage container 6 are both Pelican® brand transport cases, Model number 1620, fabricated from a proprietary fiberglass-reinforced plastic blend and having interior dimensions of approximately 22"L×17"W×13"H, and exterior dimensions of approximately 25"L×19'W×14"H. These container dimensions allow for ice water container 2 and storage container 6 to be transported on commercial aircraft. For tubes connected to heat exchanger 16, it is preferable to use ¾" internal diameter Shields® mutiflex hose, and for tubes that may be clamped, it is preferred to utilize ⅜" internal diameter and ½" external diameter platinum cured silicone tubing. All other tubes can be Clearflex® 60 transparent vinyl tubing, having a ⅜" internal and ⅝" external diameter. Biocompatible liquid tank 5 is preferably a molded seamless polycarbonate container distributed by Master-Carr® that is about ⅛" thick and rated for a 12 quart capacity. Reservoir 21, pump platform 13 and pump tray 14 are preferably made of ¼" ABS plastic. Preferably, infusion pump 51 and suction pump 52 are Flo-Jet®, "Quiet Quad" automatic multi-fixture pumps, model 4406-143, Type IV, 12 volt, 2.0 to 7.0 amp., 3.2 GPM, and rated for a maximum pressure of 35 PSI; and ice water jacket pump 52 is a FloJet®, Type H, Model LF122202, 12 volt, 3.5 amp and rated for a maximum flow rate of 1.1 GPM. The quick release fittings are preferably from Colder Products Company, identified as model No. HFC12 polypropylene of ⅜" size, and check valve 29 is a ½" ball check valve, part number 0050-BCTOO, from Thermoplastic Valves. Heat exchanger 16 is preferably a Lytron LL510 heat exchanger, manufactured by Lytron, Inc., and ice water pump 15 and return pump 24, which are in connection with heat exchanger 16, are both submersible centrifugal bilge pumps manufactured by Johnson Pumps of America (Model No. L-650). Refill pump 22 is also submersible centrifugal bilge pump manufactured by Johnson Pumps (Model No. L-450). Sensors 30, 68, and 69 are preferably all polypropylene vertical-mount liquid-level switches, manufactured by Innovative Components (Model No. LS-14-180). Endotracheal tube 12 is preferably a 9.0 mm I.D. diameter Rueschlit Super Safety, Armoured Tracheal Tube (#104004) from Willy Ruesch AG in Germany. Filter 9 is preferably a "Terumo Capiox" 40-micron arterial vented plastic bypass filter from Terumo Medical, Somerset, N.J. Air bag 10 can be a 2.6 L adult resuscitator hand-bag unit (07-870100) from Laerdal Medical Corporation, New York, with a 1-way patient gas valve (07-510112).

Preliminary Canine Experiments:

Extensive canine experiments were conducted by the inventors in order to ascertain the most effective and safest manner in which canine core temperatures could be reduced by cycling perfluorocarbon, as the biocompatible liquid, into and out of the lungs. In these experiments it was demonstrated that lung lavage with cold perfluorocarbon transferred the maximal amount of heat from the lungs of the animal on a timescale of at least as fast as the lavage could be administered and withdrawn, up to rates of at least 50 mL per kilogram of canine body weight per minute. In these experiments no waiting time was needed between the time the lavage was delivered into the lungs, and the time it was removed. It was also shown that only a fraction of the thermal content of the lavage, typically about 50%, equilibrated with the animal, but that this fraction was very little influenced by residence time in the lung, on a time scale of a few seconds to a few tens of seconds, which was typical of delivery and removal time of a lavage. For these reasons, it was thought that maximal heat transfer over time took place without any residence time between the delivery and removal of lavage volumes, with the lavage removed from the lung as quickly as possible after being introduced.

These experiments, however, were done using a method which that did not coordinate gas ventilation and liquid lavage. One reason for this was because of severe constraints in how fast lung lavage with perfluorocarbon could be delivered and removed using the Prior Device described in the Background section of this application. Also, it was also thought, incorrectly, that lavage volumes would be required to be several times the amount of mechanical dead space in the dog respiratory system (i.e., several times 6 mL/kg) in order to minimize the "thermal dead space" which was seen when small volumes of perfluorocarbon (on the order of 9 mL/kg or less) did not transfer heat as efficiently as larger lavages (20 mL/kg). Only when a series of experiments using lavage volumes as small as 3 mL/kg demonstrated a heat exchange that was comparable to the higher lavage volumes per weight of the animal, was it realized that proper coordination of lavage and gas ventilation could effectively transfer heat from smaller infusion volumes. The inventors believe that the reason was due to an increased efficiency in liquid removal with the correct type of suctioning, coupled with turbulence in the delivered and removed liquid. Such turbulence corresponds, in terms of heat transfer, to the familiar elimination of dead space by "high frequency ventilation" or "panting" in the mechanics of ventilatory mass (gas) transfer. In short, if the perfluorocarbon was delivered to and removed from the lungs quickly enough, a volume of liquid lavage was required that was much smaller than anatomical dead space in the lungs.

At the same time, a number of ways of delivering gas ventilation to the lungs were tried. As it was apparent that with the small volumes of perfluorocarbon being used (as small as 3 mL/kg) that coordinated gas ventilation (normally 10 mL/kg per breath) could and would supply most of the gas exchange, then the key question was how to supply the quantity of lung gas ventilation that would be required to keep the $CO_2$ levels in the animal's blood at normal levels. If the gas used was pure oxygen, it was found that $CO_2$ removal was the limiting factor in ventilation. $CO_2$ removal is much more sensitive to low gas ventilation volumes than oxygen level in these circumstances, just as it is with total liquid ventilation. This occurs because at the low levels of $CO_2$ (4 to 5% or 40 mmHg partial pressure) which occur in normal expired gas, the amount of $CO_2$ in a volume of either gas or perfluorocarbon is always small, when compared to the amount of oxygen contained in ventilatory gas or liquid if 100% oxygen is used. We also found in a series of experiments that about 100 mL/kg/min of gas ventilation per minute alone was needed to normalize $CO_2$ in anesthetized 20-25 kg dogs. This could be delivered in as few as 4 breaths/min of 25 mL/kg for each breath, but slower rates required breath volumes which resulted in unacceptable ventilatory pressures (>25 cm $H_2O$) when liquid was present in the lungs. Also, we found that 100 mL/kg/min of gas (oxygen) ventilation was not quite sufficient to maintain normal $pCO_2$ during liquid ventilation, and $pCO_2$ rose to 50 to 60 mmHg after 18 minutes of lavage, even with small (3 mL/kg) lavages.

A series of coordinated experiments with 3 mL/kg perfluorocarbon lavage and 25 mL/kg gas ventilation was initiated and found to give efficient heat transfer, but the relatively slow liquid lavage rate (3 mL/kg×4 lavages/min=12 mL/kg/min) resulted in relatively slow rates of cooling of minus 0.25 C/min. However, the rate of perfluorocarbon return available with the type of device being used (not the presently described device) limited the lavage rate to 12 mL/kg/min for this size animal. In the MMLV patent and later publications the inventors described cooling rates up to minus 0.5 C.°/min with larger lavage rates (liquid ventilation rates) up to 36 mL/min. However, this rate of lavage required relatively large infusions of 19 mL/kg in order to take advantage of the rapid return suction of infusion liquid which is possible when the liquid contains few gas bubbles (as happens with large lavage volumes). This is because liquid without bubbles is easier to pump or suction. This rapid return was not possible with Prior Device with small lavage volumes, or with subsequent devices, until the implementation of heat exchange apparatus 1 increased suction efficiency in the manner described in this application. Large lavage volumes of 20 mL/kg as described in the previous MMLV patent also required a relatively slow infusion delivery due to the size of the lavage (1.6 lavages/min), and thus discoordination of lavage and gas ventilation in time.

With the availability of rapid lavage liquid suction in heat exchange apparatus 1, it became possible to coordinate gas ventilation to lavage, but also to use relatively small lavages of 6 mL/kg with large amounts of gas (20 to 25 ml/kg), yet remove and infuse them sufficiently rapidly to perform 7.5 lavages/minute and 7.5 gas breaths per minute. This resulted in a liquid lavage rate of about 6×7.5 mL=45 mL/minute, and cooling rates of approximately 1 C/min. Since efficiency was maintained, the factor of 4 in lavage rate resulted in about the same factor of 4 improvement in cooling rate over the coordinated breath/lavage dogs which received 12 mL/kg/min of perfluorocarbon. In addition, ability to perform 7.5 lavages per minute offered the opportunity of performing 7.5 gas breaths of 500 mL per minute (3750 mL/min oxygen), which in a 25 kg dog is 150 mL/kg/min gas ventilation. This increase was enough to offset the diffusion barrier seen for $CO_2$ in liquid ventilation, and to result in normal levels of $CO_2$ of 40-45 mmHg during liquid lavage.

With loss of the constraint of a minimal lavage volume needed for good efficiency of heat transfer, it proved possible to coordinate smaller liquid lavages at effective breathing rates. At the same time, a series of experiments showed that small lavages of perfluorocarbon fluid, of about the FRC in volume, transferred heat maximally quickly, with the least increase in pressure and the least damage to the lung, when the lavages were administered as the lung was being simultaneously inflated by a breathing gas, preferably with 100% oxygen, as the lavage fluid was being introduced simultaneously. Less pressure was required to inflate the lungs if the inflation volume was a mixture of gas and liquid, than if the volume was liquid alone, presumably because simultaneously introduced gas is able to find, and recruit, non-dependent volumes of the lung which are not accessed by the much heavier liquid. Furthermore, it was found that heat transfer is more efficient in the dorsal recumbent dog than the dog in the lateral or ventral recumbent (prone) positions, presumably due to the larger surface area of dependent lung available to a heavy liquid, in a dorsally recumbent animal.

A number of commercial perfluorocarbons were tried for these experiments, and Fluorinert™ liquid FC-84 (perfluoroheptane) and Fluorinert™ liquid FC-40 (perfluorotributylamine) from 3M™ were both found to be acceptable liquids for use as the biocompatible liquid used in the experiments. Commercial Perflubron™ is not suitable for liquid lavage at the liquid temperatures used in the experiments because it freezes at 4° C. and is too viscous to be useable below 15° C.

An additional series of experiments showed that delivery of cold perfluorocarbon directly into the major tracheal branches of lung with small (12 F) catheters, followed by distal removal of liquid in from these catheters, or even distal infusion of fluid, followed by removal from a single catheter in the upper trachea, did not increase the efficiency of heat transfer of lavages. At net rates of lavage of 12 mL/kg/minute of perfluorocarbon (infusion rate 60 mL/kg/min, fluid suction rates up to 25 mL/kg/min), efficiency of heat exchange did not rise above 60% (Abstract poster presented at Society for Critical Care Research meeting, 2002). However, these experiments did show that dogs could be cooled by −3° C. in less than 30 minutes. The relatively slow cooling rate in the above experiments (0.1 C/min) could have been doubled by maximally chilling infused perfluorocarbon to 1-2° C., but a further limit at 0.2° C./min was caused by the relatively small rates of absolute suction which can be applied though small tubes (500 mL/min absolute). This contrasts with the 2 to 3 L/min suction which can be obtained for liquid from conventional flatwire venous drainage cannulae, such as the 17 F Biomedicus™ brand canulae used for surgical femoral artery bypass.

Furthermore, it was found that high speed jet delivery of cold perfluorocarbon to the distal ends of the trachea caused evidence of damage, as hemorrhage was seen in the trachea on necropsy at 24 hours, corresponding to the tip ends of the 12 French catheters. This damage disappeared when perfluorocarbon was merely introduced into the upper end of the endotracheal tube. In this case, to prevent perfluorocarbon overflow, the lung was merely required to be inflated with oxygen gas ahead of the perfluorocarbon. When this was done, a flow of cold perfluorocarbon that was introduced into the top of the endotracheal tube dropped into the lungs and was further spread by an insufflated breath of oxygen into the interior sections of lungs where heat exchange took place.

In a similar fashion, attempts to minimize fluid dead space in the lungs by putting small suction catheters at the ends of the bronchi where not ultimately successful as methods of increasing net rate of heat transfer. This was, in part, due to the fact that the small diameter of the catheters limited the rate at which fluid could be removed from the lungs, and this limitation proved to further limit the rate of heat transfer, because it limited rate of liquid transfer. Eventually, in suction, it was found that the single greatest assistance to time-efficient removal of fluids from the lungs, and thus in time efficient transfer of heat, lay in application of gentle negative pressure so that the lungs were collapsed, as at the end of a forced exhalation. This made maximal fluid from the lungs available, as at the end of a squeezed sponge, and this fluid could be picked up at the end of a normal endotracheal tube, situated relatively high up in the trachea, and carried out by suction.

In summary, the inventors realized that a device which introduced fluid to the top of an endotracheal tube at the same time a gas breath was applied, and then removed both gas and liquid from the top of the tube while suction was applied to the entire cuffed tube, adequately performed both the job of administration and removal of liquid from the lungs. No second luminal tube, as in the Prior Device described in the Background section of this application, was needed. By this reasoning, and with significant empirical experimentation, a time-efficient technique for maximal heat transfer from small lavages of perfluorocarbon within the lung of a canine was eventually developed, and implemented in portable heat exchange apparatus 1.

Use of Apparatus:

In test experiments with 5 canines, the portable heat exchange apparatus 1 was used to successfully lower the core temperature of the dogs by cycling a volume of 6.0 to 9.3 ml of perfluorocarbon per kilogram body weight of the animal into and out of the lungs of the animal at a cycle rate of 1 cycle approximately every 8 seconds, with a delivery period of approximately 3.5 seconds and a removal period of approximately 4.5 seconds. Each test experiment was carried out in accordance with the following procedure. If pump assembly 7 and tube assembly 8 have not be connected to ice water container 2 and biocompatible liquid tank 5 but are stored in storage container 6, the operator opens the lid to storage container 6 and removes the two assemblies and pump tray 14 from container 6. In this regard, although tube assembly 8 as identified in the figures includes endotracheal tube 12, the endotracheal tube would be normally stored in a sterile container separately from the other components of tube assembly 8. The operator then closes the lid, attaches frame 89 to the underside of storage container 6, places ice water container 2 on top of storage container 6, and secures the two containers with clamp assemblies 89. The operator starts preparing apparatus 1 for use by adding approximately 15 liters of water and 10 kilograms of ice to ice water container 2, and by adding 6 liters of a biocompatible liquid, which in all experiments was perfluorocarbon, to biocompatible liquid tank 5. The operator then starts cooling the perfluorocarbon in tank 5 by supplying power to the heat exchanger pumps by connecting wiring 4A to socket 99 and connecting wiring 4B to socket 98, and then turning on heat exchanger pumps switch S6 on control panel 4, which activates ice water pump 15 and return pump 24. This causes ice water to flow from ice water pump 15, through tube 17A, through heat exchanger 16 where the temperature of the ice water increases due to heat exchange, through tube 17B, and out of sprayer 18, which returns the warmed ice water to ice water container 2. Sprayer 18 diffuses the returning warmed ice water in order to increase the efficiency of re-cooling the warmed ice water by distributing the warmed ice water over the surface of the ice cubes and ice water 19 in ice water container 2. At the same time, perfluorocarbon flows from return pump 24, through tubes 41A and 41B, through heat exchanger 16 where the temperature of the perfluorocarbon is reduced due to the transfer of heat between the perfluorocarbon and the ice water, through tube 41C and out of an open end of tube 41D which returns the cooled perfluorocarbon to tank 5.

While the perfluorocarbon is being cooled, the operator places pump assembly 7 upon pump tray 14, which in turn is placed upon the top of ice water container 2 and connects the pumps within pump assembly 7 to biocompatible liquid tank 5, as described above, and the operator connects tube assembly 8 to pump assembly 7, as also described above. Next, the operator turns on switch S7, activating ice water jacket pump 53, causing ice water to be delivered to tube assembly 8 by passing through supply tube 43A within ice water supply assembly 80, through ice water supply tubes 43B, 43C, 43D, within pump assembly 7, and through ice water supply tube 43E within tube assembly 8. The ice water returns from tube assembly 8 by passing though return tubes 44B and 44A and into ice water container 2. At this point, an anesthetized dog that has been placed on an operating table next to apparatus 1 is intubated using endotracheal tube 12. While the dog is being intubated, another operator uses control panel 4 to set infusion/suction cycles. Based upon extensive preliminary testing described above it has been determined that apparatus 1 is capable of delivering and removing a volume of perfluorocarbon to and from the lungs of the dogs weighing up to 27.5 kilograms at a rate of 1 cycle or lavage approximately every 8 seconds, with an infusion time period of approximately 3.5 seconds and a suction time period of approximately 4.5 seconds. As a result, the operator would normally use rotary switch 92 on control panel 4 to set the total perfluorocarbon infusion time at 3.5 seconds, representing the elapsed time between when infusion pump 51 starts delivering cooled perfluorocarbon to the lungs and when the pump stops delivering perfluorocarbon. Next, using rotary switch 93, the total cycle time of 8 seconds is set, which is equal to the total infusion time, plus the elapsed time between when suction pump 52 starts removing warmed perfluorocarbon from the lungs and when the pump stops removing perfluorocarbon. Next, the operator establishes the desired volume of perfluorocarbon that is to be delivered to the lungs during each infusion cycle. This is accomplished by adding or removing an appropriate number of volume displacement tabs 60 to infusion reservoir 21. The tabs 60 are sized in various thicknesses so as to displace a wide range of fixed volumes of liquid in reservoir 21. As set forth in the following table, reservoir 21 and tabs 60 are sized such that the following biocompatible liquid volumes can be added to tank 5 and delivered to the lungs on each infusion cycle:

| To deliver this infusion volume: | Insert tabs having these thicknesses: | | | | |
|---|---|---|---|---|---|
| | 2" | 1" | ½" | ¼" | ⅛" |
| 110 ml | yes | yes | yes | yes | yes |
| 125 ml | yes | yes | yes | yes | no |
| 145 ml | yes | yes | yes | no | yes |
| 160 ml | yes | yes | yes | no | no |
| 180 ml | yes | yes | no | yes | yes |
| 195 ml | yes | yes | no | yes | no |
| 215 ml | yes | yes | no | no | yes |
| 230 ml | yes | yes | no | no | no |
| 300 ml | yes | no | yes | no | no |
| 370 ml | yes | no | no | no | no |
| 510 ml | no | yes | no | no | no |
| 650 ml | no | no | no | no | no |

In this regard, it has been determined by the inventors that based upon extensive preliminary testing that the most effective volume of perfluorocarbon at the cycle rate describe above is between about 6 and 9 mL/kg of animal body weight. As a result, the operator would first determine the weight of the animal and then select the number of tabs that would deliver the appropriate volume of perfluorocarbon. If an infusion volume below 400 mL is used, the operator should partially tighten screw-clamp 35 to constrain the flow of liquid from refill pump 22 via tube 28 to reservoir 21. Constraining the flow is desirable to prevent surging of liquid in reservoir 21 when its effective volume has been decreased by adding displacement tabs. Surging of liquid causes inaccurate behavior of high-level float sensor 67.

As soon as these preparations are completed and the dog has been instrumented to record temperature and other experimental data, the operator turns switch S8 to its manual position and primes the system by using switch 9 to pump liquid through infusion tubes 42A, 42B and 42C, infusion pump 51, infusion tubes 42D and 42E, and "Y" fitting 46, and into a graduated cylinder. The operator then uses switch 9 to suction liquid back from the cylinder, through suction tubes 40A and 40B, suction pump 52, and suction tubes 40C and 40D, and repeats these cycles until all tubing in the system is fully loaded with liquid. "Y" fitting 46 is then attached to the open end of endotracheal tube 12 which is protruding from the animal's mouth.

The transfer of liquid from biocompatible liquid tank 5 into the tubing of the apparatus may result in liquid level 20 in tank 5 falling below its minimum acceptable level, in which case tank level sensor 30 will cause an alarm to sound, and the operator must add more liquid to tank 5 until the alarm stops sounding.

Heat exchange is started by using switch S8 to select auto mode which automatically starts continuously cycling the cooled perfluorocarbon into and out of the animal's lungs. During each suction cycle refill pump 22 is activated and replenishes reservoir 21 with cooled perfluorocarbon liquid. Pump 22 is automatically turned off when the rising level of perfluorocarbon in reservoir 21 activates upper level float sensor 67. At the end of each suction cycle, infusion pump 51 is activated and cooled perfluorocarbon flows out of reservoir 21, through infusion tubes 41A though 42E, through filter 9, through tubular "Y" fittings 45 and 46, and through endotracheal tube 12 and into the lungs. Just prior to each infusion of perfluorocarbon, however, the operator relaxes clamp 33 attached to tube 34 that opens and airway leading from air bag 10 to the lungs of the animal, and the operator begins to gently compress the bag with his or her hands, thereby supply a breath of oxygen to the lungs as the perfluorocarbon is being infused. This action causes oxygen to mix to some degree with the perfluorocarbon within endotracheal tube 12, and additional mixing occurs when the perfluorocarbon and oxygen enter the lungs. Although it is preferable for the operator to use air bag 10 to deliver a breath of oxygen to the lungs at the same time that the perfluorocarbon begins to be delivered to the lungs, the operator has complete control over when and how much air is delivered and can depart from the preferred procedure when, for example, the operator senses with his or her hands that too much pressure has built up in the lungs. Higher pressure in the lungs can occur when, for what ever reason, a leak within the tubing or the tubular connection to the endotracheal tube reduces the amount of perfluorocarbon that is removed from the lungs. As soon as infusion pump 51 is turned off and perfluorocarbon stops flowing into the lungs, suction pump 52 is again activated and the perfluorocarbon that has been warmed in the lungs is removed from the lungs and it flows back through endotracheal 12 and tubular fittings 46 and 45 and then through suction tubes 40A through 40D, where the perfluorocarbon cascades down from an end of tube 40D until it reaches the level 20 of perfluorocarbon in tank 5, above the opening in inlet pipe 26. As described above in connection with FIG. 9, the returning warm perfluorocarbon liquid is directed into pump manifold 23, which re-circulates the liquid through the heat exchanger 16 and returns the liquid to tank 5, where it mixes with the perfluorocarbon in tank 5. The delivery and removal cycles are continuous cycles in that there is not any significant delay between each delivery of the perfluorocarbon and its removal and the start of the next cycle. While heat exchange is proceeding, high-level float sensor 67 will shut off refill pump 22 when the predetermined volume of perfluorocarbon has been delivered to infusion reservoir 21, and low-level sensor 68 will stop the infusion pump if the desired volume has been infused in a shorter time than was set by rotary switch 92. Further, after a significant amount of the ice in ice water container 2 has melted, which can be readily observed by the operator, more ice can be easy added to ice water tank 2 while heat exchange is proceeding. This is carried out by first draining some of the water from ice water container 2 by using a drain tube connected to quick disconnect 43F and then manually adding more ice to the container.

Figure 17:
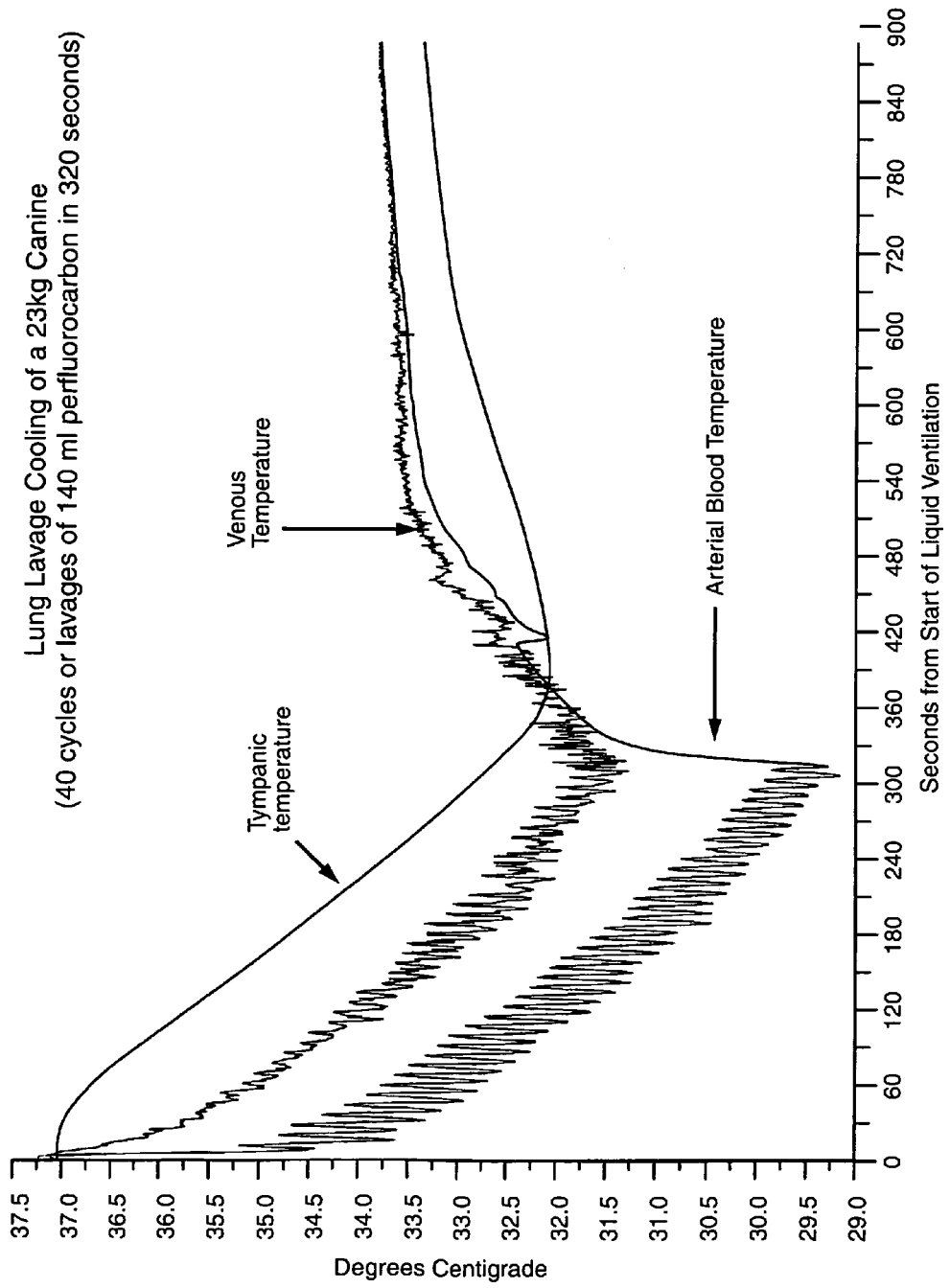
FIG. 17 is a graph illustrating the results of using the portable heat exchange apparatus to administer heat exchange within the lungs of a canine.

FIGS. 17 and 18 presented the cooling rates over time that were achieved using heat exchange apparatus 1 to administer cold perfluorocarbon to the five dogs using the procedure outlined above. Again, all experiments were carried out by delivering perfluorocarbon at a cycle rate of 1 cycle approximately every 8 seconds, with the perfluorocarbon being delivered within approximately 3.5 seconds and being removed within approximately 4.5 seconds. Referring first to FIG. 17, the figure presents a graph of cooling rates, in which perfluorocarbon was continuously cycled into and out of the lungs of a 23 kg dog. A total of 40 cycles were administered over a heat exchange period of 320 seconds, when heat exchange was terminated. One line on the graph, labeled "tympanic Temperature", illustrates that the dog's brain temperature, as measured tympanically, dropped about 4° C. within the 320 second period during which heat exchange was administered to the animal. Another line on the graph, labeled "Venous Blood Temperature", shows that the animal's venous blood temperature was reduced by almost 6° C. within the same time period. A third line, labeled "Arterial Blood Temp", shows a drop in temperature in which the arterial blood temperature was reduced approximately 8° C. within the heat exchange period.

FIG. 18 presents a graph of tympanically measured brain temperature cooing rates for four canines, in which perfluorocarbon was continuously cycled into and out of the lungs of the dogs, again at a cycle rate of 1 cycle approximately every 8 seconds, with the perfluorocarbon being delivered within approximately 3.5 seconds and being removed within approximately 4.5 seconds. A 23.3 kg dog received 6 ml of perfluorocarbon per kilogram of dog body weight or a total of about 140 ml of perfluorocarbon per infusion cycle, and the perfluorocarbon was continuously cycled into and out of the lungs over a period of 10 minutes. A 20.0 kg dog received 6.5 ml of perfluorocarbon per kilogram of dog body weight or a total of 130 ml of perfluorocarbon per infusion cycle, and the perfluorocarbon was continuously cycled into and out of the lungs over a period of 10 minutes. 27.5 kg dog received 6.0 ml of perfluorocarbon per kilogram of dog body weight or a total of 165 ml of perfluorocarbon per infusion cycle, and the perfluorocarbon was continuously cycled into and out of the lungs over a period of 15 minutes. And, a 20.4 kg dog received 9.3 ml of perfluorocarbon per kilogram of dog body weight or a total of about 190 ml of perfluorocarbon per infusion cycle, and the perfluorocarbon was continuously cycled into and out of the lungs over a period of 15 minutes. The two dogs that both received lung lavages for 10 minutes exhibited a drop in brain temperature of approximately 8° C. or about twice the total cooling exhibited by the dog that received lung lavage for just over 5 minutes as shown in FIG. 17. The 27.5 kg dog that received lung lavages for 15 minutes exhibited a drop in brain temperature of approximately 9° C., and the 20.4 kg animal showed a brain temperature drop of almost 11° C. These results show that cooling rates are approximately constant for the first 10 minutes but then start to significantly slow down for longer time intervals.

In all of the animals, after heat exchange was terminated the animals were allowed to thermally equilibrate for a period of time, and then temperature and pressure cannulae were removed from their arteries and veins, their incisions closed, and they were removed from anesthesia. The endotracheal tubes were removed as soon as the animals started breathing normally on room air. Typical blood gases on room air resulted in pO2 of about 250 mmHg on 90% oxygen post lavage (about 450 to 500 mmHg pre-lavage) and normal pCO2 in the 40 mmHg range. Post lavage oxygen on air was typically 70 mmHg, for an increased A-a gap of about 30 mmHg. Saturation was typically >90% on room air (tongue pulse oxymetry).

Abnormality of breath sounds post lavage usually consisted only of expiratory breath sounds in all lobes, approximating that of inspiration (i.e., mild obstruction, in as much as expiration was no longer quiet). Some dogs had mild increases in expiratory time, and diaphragmatic breathing. However, all animals were up and walking, eating and drinking by the following day ("day two"). They also showed no signs of abnormal behavior on day two. Lung sounds in some animals normalized on day two, but other animals continued to show mild obstructive sounds, without gross wheezing. Chest X-rays showed a very mild alveolar diffuse infiltrate pattern immediately post-lavage with perfluorocarbon FC-84, which was gone at day two. The mild infiltrate pattern with perfluorocarbon FC-40 persisted at day two. No pneumothorax or fluorothorax was seen.

Three of the five animals were euthanized at 48 hours for lung examination, blood gasses had not changed significantly. The animals were anesthetized, perfused with saline, then formaldehyde fixative to replace blood. Lungs, when removed, showed a few petechial hemorrhages, but no major damage or hemorrhage, and excellent washout of blood. When fully inflated by endotracheal tube, they had no tears or leaks of air. Retained perfluorocarbon was seen as a slightly yellowish discoloration in lung dependent lobes, against the white of normal lung. When lungs were fully inflated, this discoloration tended to be overridden by the lightness caused by air expansion of lung. The other two animals are still alive a about year after the experiments, and they have not exhibited any noticeable side effects from the procedure.

Emergency Use:

In addition to the veterinary use described above, portable heat exchange apparatus 1 can also be used to reduce the body temperature of humans. It is known that the size of human lungs is approximately 75% the size of canine lungs for the same body mass. Using this scale, it is anticipated that infusion volumes of approximately 6 mL/kg of human body weight (representing about ⅓ of the functional residual capacity (FRC) within a human lung) and cycle rates of 1 cycle approximately every 8.0 seconds would be safe and effective. In this regard, it is anticipated that the most useful application of portable heat exchange apparatus 1 to humans would be in an emergency situation where it is critical to safely reduce a patient's body temperature as quickly as possible. Accordingly, portable heat exchange apparatus 1 can be used by paramedics or other emergency personnel to transport apparatus 1 by ambulance to the location of a patient who is, for example, suffering from cardiac arrest and to quickly and efficiently administer heat exchange to the patient's lungs as soon as the emergency personnel arrive at the scene and have restarted the heart, and while the patient is being transported by ambulance to a medical facility. Alternatively, the apparatus 1 can be transported by aircraft or helicopter to a remote location, such a forest fire site or a war zone, where it is anticipated that the apparatus 1 may be needed by patients suffering from heat stroke and who are too far away from a medical facility with skilled and licensed physicians having access to more elaborate and sophisticated equipment and services. Further, apparatus 1 has a cryogenics application in that it can be used to reduce the temperature of a person's body until it can be cryogenically preserved.

In the ambulance deployment scenario, the portable heat exchange apparatus 1, in its transportable configuration as shown in FIG. 11, is wheeled into the ambulance as soon as the paramedics are notified of, for example, a case of cardiac arrest. During transit to the patient's location, the paramedics disconnect storage container 6 from ice container 2 and remove pump assembly 7 and tube assembly 8, including its endotracheal tube 12, from the storage container and connect assemblies to ice container 2 and reservoir tank 5. The paramedics then begin preparing the apparatus 1 just as described above for its use with canines by adding approximately 15 liters of water and 10 kilograms of ice to ice water container 2, and by adding 6 liters of perfluorocarbon to biocompatible liquid tank 5. Then they start cooling the perfluorocarbon in tank 5 by turning on switch S7 to activate ice water pump 53 and turning of switch S6 to activate ice water pump 15 and return pump 24. In addition, if the paramedics have time before reaching the patient, they would prime the system in order to remove air in the tubing. The priming operation is performed by first clamping tube 47 so as to prevent the biocompatible liquid coming from reservoir 21 to flow out of "Y" fitting 46, thereby creating a closed system. Switch S8 is placed in manual mode and then switch S10 is pressed down for about 30 seconds, causing the biocompatible liquid to cycle through the closed system, rather than to the patient. In this priming mode, infusion pump 51 and suction pump 52 both run continuously in order to remove the air as fast as possible, and refill pump 22 runs continuously in order to maintain the level of biocompatible liquid in reservoir 21. Priming is stopped by releasing Switch S10 and returning switch S8 to is off or center position. Alternatively, the paramedics can prime the system when they reach the patient, or in an extreme emergency start heat exchange without priming the system.

When the ambulance reaches the patient, the portable heat exchange apparatus 1 is wheeled on a ramp out of the ambulance and rolled into position next to the patient, who is placed on a gurney and intubated by a paramedic using endotracheal tube 12, which is then connected to "Y" fitting 46. While the patient is being intubated, another paramedic uses control panel 4 to set infusion/suction cycles, which preferably would be the same as those cycles described in the canine experiments. At this point, the paramedics are required to estimate the weight of the patient, which is an essential skill of all licensed paramedics. Once the patient's weight is estimated, the paramedic uses volume displacement tabs 60 in order to establish the perfluorocarbon infusion volume. This is accomplished by adding or removing an appropriate number of volume displacement tabs 60 to infusion reservoir 21. Tabs 60 are sized in various thicknesses so as to displace a fixed volume of liquid in infusion reservoir 21. More specifically, tabs 60 are sized such that for a given patient's bodyweight either a small, medium, large and/or extra-large displacement tab 60 is positioned in infusion reservoir 21. If the patient weighs 108 kilograms or more, no displacement tabs are used. The following table presents several displacement tab combinations to deliver a fixed volume of perfluorocarbon to a patient based upon the delivery of 6.0 mL/kg of perfluorocarbon per body weight of the patient:

| Patient Weight: | Include these tabs: | | | |
| --- | --- | --- | --- | --- |
| | small | medium | large | x-large |
| 108 kg (or more) | no | no | no | no |
| 102 kg | yes | no | no | no |
| 96 kg | no | yes | no | no |
| 90 kg | yes | yes | no | no |
| 84 kg | no | no | yes | no |
| 78 kg | yes | no | yes | no |
| 72 kg | no | yes | yes | no |
| 66 kg | yes | yes | yes | no |
| 60 kg | no | no | no | yes |
| 54 kg | yes | no | no | yes |
| 48 kg | no | yes | no | yes |
| 42 kg | yes | yes | no | yes |
| 36 kg | no | no | yes | yes |
| 30 kg | yes | no | yes | yes |
| 24 kg | no | yes | yes | yes |
| 18 kg | yes | yes | yes | yes |

For example, for a patient weighing 54 kg a small and extra-large sized tab would be disposed within infusion reservoir 21, which would result in delivering 324 ml to the lungs of the patient on each infusion cycle.

As soon as these preparations are completed, heat exchange is started by unclamping tube 47 and using switch S8 to select auto mode which automatically starts cycling the cooled perfluorocarbon into and out of the patient's lungs, and the apparatus operates just as described in the canine experiments. As soon as heat exchange has been started, the patient and the portable heat exchange apparatus 1 are rolled in tandem back to the ambulance where the heat exchange and liquid ventilation can be continued until the patient is delivered to a medical facility. At that point, heat exchange can be continued with heat exchange apparatus 1 or it can be quickly disconnected and more sophisticated equipment and procedures can be used to cool down the patient's body temperature.

In the second scenario, heat exchange apparatus is delivered by air carrier to a location where it is anticipated that it might be needed. Once at the location, the apparatus can be assembled and easily wheeled into position, just as it is when removed from an ambulance, and then used in the same manner. It is anticipated that under this scenario the apparatus would be the procedure of last resort due to the remote location of its use. However, it is feasible that the patient could be transported by air while continuing to receive heat exchange therapy, just as in an ambulance scenario.

In addition to performing heat exchange within the lungs of patients, the apparatus 1 is intended for use immediately after death is pronounced to cool the person's brain and body, thus lowering the metabolic rate and reducing ischemic injury until the person can be cryogenically preserved. In this instance, the apparatus is used in the same manner as that described for a living patient; however, the apparatus could be used for much longer periods of time during which the body temperature could be lowered far below the level that would be safe for a living patient.

Thermal Calculations:

The size of individual lavages was dictated in part by how much fluid could be delivered and removed at a rate or breathing cycle of 1 cycle approximately every 8 seconds, which was the gas ventilation rate calculated to keep $pCO_2$ in the normal range in arterial blood of the animals. In this regard, oxygen saturation was typically much higher, around 250 Torr, due to the 100% oxygen gas used to ventilate. The primary limitation on lavage total rate was the amount of fluid suction that could be accomplished in the suction part of the breathing cycle, which was approximately 4.5 seconds.

In summary, the perfluorocarbon volumes described herein represent reasonable limits as to amounts of liquid which can be added and removed from the lungs of a mammal, in a normal ventilation cycle time of about 7.5 lavages per minute. As discussed below, this amount of fluid (56 to 72 mL/kg/min) is also that which is required to obtain about a 4° C. temperature drop in the brain in the first 5 minutes of post resuscitation lung lavage with ice cold perfluorocarbon.

Calculations of Heat Transfer:

The total heat capacity of mammals is about 0.7 kcal/kg/degree K. In a situation of very rapid cooling, as when done with MMLV lung lavage, only about 60% to 70% of the heat capacity (the so-called thermal core) of the animal is cooled, and this is responsible for the 30%-40% "rebound re-warming" which occurs after rapid cooling has stopped. This can be prevented by "overcooling" by 30% to 40% in the active phase of cooling. In lung lavage medical devices, a reasonable goal has been to cool the brain by minus 4° C. in the first 5 minutes of treatment. It has been argued by Dr. Lance Becker (University of Pennsylvania) that this cooling rate is necessary for maximal effect, since minus 4° C. has been the traditional amount of cooling to induce "mild hypothermia" with its many benefits in post-resuscitation, and 5 minutes is the maximal time in which the brain can survive without the beginning of ischemic damage, in the absence of blood pressure. Dr. Becker has argued that induction of mild hypothermia in this time period would provide the best chance to induce the favorable state in a time which would not be so long as to allow much ischemic damage in the post-resuscitation period.

During such a treatment which aims to drop brain temperature by minus 4 C in 5 minutes, the maximal cooling rate needs to rise to about 1.2 degrees C/min, in order to compensate for the fact that during the first 60 seconds of blood-cooling there is little temperature drop in the brain due to blood convection delay time, and it requires about 100 seconds for maximal rate of temperature drop (dT/dt) in the brain to become fully developed, after the start of rapid removal of heat from the lungs. The treatment need not be continued longer than 5 minutes if a permanent decrease in whole-body temperatures of minus 4° C. is desired, since the nadir of cooling is not reached until about 1 minute after cooling stops, and is lower than the target. After 5 minutes of treatment, then cessation of cooling, core temperature continues to drop between minus 5 to 5.5° C. at 5.9 to 6.6 minutes after the start of treatment, then rises again as the thermal compartments of the animal all equilibrate. A permanent temperature drop of about minus 4° C. may be expected once this equilibration has happened. In experiments to be presented, a wait of up to 30 minutes (1800 seconds) has been instituted to observe this equilibration after 5 to 15 minutes of lung lavage.

EQUATIONS

The total volume of perfluorocarbon per mass of animal (volume/mass) required to cool a mammal by a permanent temperature drop ($\Delta Tm$) of minus 4° C. is calculated by equating the heat added to the perfluorocarbon volume (Vf), to the heat removed from the animal. This heat (Q) is the total perfluorocarbon volume (Vf) multiplied by the volume specific perfluorocarbon heat capacity (Cv), multiplied by the difference in temperature between this perfluorocarbon volume and the mammal, $\Delta Tf$, multiplied by the efficiency E with which the heat is extracted from the perfluorocarbon in the process. This heat, given by the formula $Q=Vf*Cv*\Delta Tf*E$, is the heat gained by the perfluorocarbon. It is equal to the heat lost by the mammal, which is given by the mass-specific heat capacity of the mammal (Cm) multiplied by mammal mass m and the temperature change in the mammal. This heat lost by the mammal is given by:

$$Q=mCm*\Delta Tm.$$

Equating the two heats and solving for Vf/m (the volume of perfluorocarbon needed per kg of mammal) gives:

$$Vf/m=[\Delta Tm/\Delta Tf]*[Cm/Cv]*[1/*E] \quad \text{Eq 1.}$$

where the mean temperature difference between the perfluorocarbon and animal ($\Delta Tf$) is 33° C. and the temperature change in the mammal ($\Delta Tm$) is 4° C.; the mass-specific heat capacity of the whole mammal (Cm) is about 0.7 Kcal/kg (as shown by many experiments with various lean mammals, all showing approximately this heat capacity); and the volumetric heat capacity (Cv) of all perfluorocarbon liquids is about 0.45 Kcal/L.

The efficiency for heat transfer (E) from perfluorocarbon to mammal is a pure number which represents the amount of heat the perfluorocarbon absorbs in practice, with regard to the theoretical maximal amount it could extract in theory. An efficiency of 1 (100%) would mean perfluorocarbon would return from the animal at the brain temperature of the animal, having come to perfect equilibrium with it before being extracted. In practice, efficiency numbers for small lung lavage models with the lavage properly placed, are nearly always 50 to 60%.

In our dog model, the median thermal efficiency of small perfluorocarbon lavages has been found to be about 60% for rapid lavage and this is relatively independent of the size of the lavage. This probably represents the fact that lavage perfluorocarbon returns at a temperature which is set by the venous and arterial blood, which are minus 2.5° and 5° C. lower than the brain, respectively, and also by the fact that newly delivered perfluorocarbon drops into a "pool" of warm perfluorocarbon already in the lung, and also contacts regions of lung which cannot efficiently transfer heat to it. Both of these effects result in a kind of thermal dead space, which is represented by a volume of V(1−E) where V is the volume of infusion, and E is the efficiency.

Using these numbers the total amount of perfluorocarbon V to give a minus 4° C. permanent temperature drop (ΔT) is:

$$V=(4/33)*(0.65 \text{ kcal/kg/K}/0.45 \text{ kcal/L/K})*(1/0.60)= 0.314 \text{ L/kg}=290 \text{ mL/kg},$$

representing the amount of perfluorocarbon that will cool the animal permanently by minus 4° C., whether it is cyclically infused and removed during 5 minutes, 30 minutes, or longer. If this volume is to be given in 5 minutes at a rate of 7.5 lavages per minute, then it must be divided into 37.5 lavages, with each lavage composed of 314/37.5=7.8 mL/kg lavage. This is a lavage rate of 58 mL/kg/min.

In order to achieve cooling of minus 4° C. in the first 5 minutes of lavage, a maximal heat transfer of 1.1 C/min must be created, largely to compensate for the relative lack of transfer in the first 1 minute of the experiment. However, this rate of cooling must be achieved only for the thermal "core." These are the tissues which are very well perfused tissues, such as the lungs heart, viscera, and brain. They represent a thermal capacity corresponding to only about 68% of the heat capacity of the mammal, or about 0.47 kcal/kg/K. Thus, the maximal cooling rate (cooling only the animal core) is given by solving equation 1 above for ΔTm:

$$\Delta Tm = V \Delta Tf [Cv/Cm] E.$$

Differentiating this equation (dV/dt) gives the cooling rate expected for given a rate of lavage:

$$dTm/dt = [Cv/Cm]*E*(\Delta Tf)dV/dt.$$

Using Cm=0.47 kcal/kg/K in this calculation because of the smaller thermal (core) mass Cm being cooled during the rapid phase of cooling (ie, the whole body is not being cooled in the early phase, but only the thermal core including the brain), the rate of maximal brain cooling may be calculated. A minute-lavage rate of dV/dt=58 mL/kg/min, then the total lavage rate dV/dt per minute is given by:

$$dT/dt = [0.45/0.47](0.6)*(33)*0.058 \text{ L/min}=1.1 \text{ C/min}$$

This is maximal cooling rate which may be expected at this lavage rate.

The needed total of about 290 mL/kg perfluorocarbon must be delivered as 290/37.5=7.8 mL/kg lavages if these are to be given within 5 minutes. This should achieve a drop of minus 4° C. at 5 minutes and a permanent drop of about the same amount. However, the nadir of the temperature drop will be lower than this figures, and can be estimated by the relative size of the temporarily cooled "core" thermal capacity to final thermal capacity, which two capacities which have a ratio of 0.7/0.45=1.55. Thus, the nadir in core temperature can be expected to reach 4×1.55=minus 6.2° C. in a short cooling time experiment in which minus 4° C. decrease in 5 minutes, and also minus 4° C. permanent decrease, is the final goal. A drop of 4.6° C. against a final drop of minus 3.7° C. was actually seen (ratio of 1.24). If smaller lavage size is used, the cooling rates in theory will be reduced proportionally. For example, if 6.1 mL lavages are used, as is the mean lavage size 4 of 5 of the animals shown in FIGS. 1 and 2, then cooling rates and final amount of cooling might be expected to be 6.1/8.4=73% expected in the calculation above. In the dog shown in FIG. 1, lavage at the rate of 45 ml/kg/min was performed, and maximal cooling rate of minus 0.92° C./min was observed, as compared to 1.1×78%=minus 0.86° C./min expected. The final temperature drop in this animal, which was lavaged for slightly longer than 5 minutes (5.25 min) was minus 3.7° C. The total lavage delivered was 6 mL/kg×40 lavages=240 mL/kg. The expected temperature drop was minus 4° C. (240/290)=3.3° C. against the drop of 3.7 C actually observed.

Advantages:

Using portable heat exchange apparatus 1 to reduce the core body temperature of a mammal has several advantages over the Prior Device disclosed in the MMLV patent. Most significantly, apparatus 1 has demonstrated the ability to reduce core body temperature by about 4° C. in approximately 5 minutes, which represents an increase in cooling rate during that time of almost 300% over the Prior Device. Apparatus 1 has been able to achieve this substantially increased cooling rate due to several unique design features that have been incorporated into the apparatus. One feature is that the perfluorocarbon is delivered to the lungs of the mammal through a single endotracheal tube in that the use by the Prior Device of a separate infusion/suction tube concentrically disposed within its endotracheal tube has been eliminated. This change has substantially increased the tubular cross-sectional area for delivery of the perfluorocarbon, thus facilitating the delivery of much higher volumes of perfluorocarbon. This change has also provided for the elimination of the oxygenator used in the Prior Device to remove CO2 from the perfluorocarbon being removed from the lungs, because the Prior Device delivered a volume of gas ventilation that was 2 to 3 time larger than the volume of the perfluorocarbon being delivered at the same time. This amount of gas ventilation renders the amount of ventilation delivered and removed by the dissolved gases in the lungs as inconsequential. In consequence, direct oxygenation and CO2 stripping of the perfluorocarbon liquid is not necessary with the relatively small lavage sizes (6 to 9 mL/kg) delivered with the relatively large gas breaths (mean of 21 mL oxygen/kg for this group with mean weight of 23 kg). In addition, the perfluorocarbon being delivered to the lungs is substantially cooler than the perfluorocarbon that was delivered by the Prior Device. This additional cooling is provided by several other unique features. The Prior Device stored the perfluorocarbon in a container that was separated from an ice water slurry and transferred the perfluorocarbon through tubing to the heat exchanger. The present apparatus disposes or nests biocompatible liquid tank 5, which contains the biocompatible liquid, inside of ice water container 2, which contains ice water 19. In this manner, apparatus 1 is able to eliminate the long tubing between the two containers as in the Prior Device and replaces the tubing with much shorter tubes that are submerged in ice water 19. Submerging the tubing in ice water 19 provides a superior insulator to the foam insulation used to insulate the tubing in the Prior Device. Similarly, surrounding biocompatible liquid tank 5 with ice water 19 also provides a much more effective manner of keeping the biocompatible liquid cool, rather than using foam insulation as in the Prior Device. Another deficiency of the Prior Device is that it used only foam insulation surrounding the long tubes that delivered the biocompatible liquid from its container to the lungs of the mammal. Apparatus 1, on the other hand, circulates some of the ice water from ice water container 2 through tube assembly 8, which further includes an insulation jacket assembly 36 surrounding the tubing within the assembly. Again, the circulating ice water provides substantially more insulation than only the foam used in the Prior Device.

In addition to the substantially improved heat exchange characteristics, apparatus 1 is portable and easy to use in an emergency. Portability is provided, in part, by the unique nesting of biocompatible tank 5 within ice water container 2 and by the modular design of pump assembly 7 and tube assembly 8, which greatly facilitate storage of the components in storage container 6 and the ease with which apparatus 1 can be assembled in an emergency. Mobility is provided by mounting the ice water and storage containers on removable wheeled frame 89. Portability is further enhanced by eliminating the large, computer controlled ventilator use in the Prior Device with air bag 10 that is manually operated to supply oxygen to the mammal. In addition to being extremely light compared to the computer controlled ventilator, manual operation allows the operator to use his or her hands to sense when the lungs are filled to capacity, thereby avoiding the potential that that lungs might be over inflated by the computer and causing severe damage to the lungs.

Although the portable heat exchange apparatus and method has been described in its preferred embodiment and in certain other embodiments, it will be recognized by those skilled in the art that other embodiments and features may be provided without departing from the underlying principals of those embodiments. The scope of the invention is defined by the appended claims.

We claim:

1. An apparatus for the administration of heat exchange in the lungs of a mammal by cyclically delivering and removing a biocompatible liquid to and from the lungs, comprising:
   a) an ice water container having an open top end and adapted for containing ice water;
   b) a biocompatible liquid tank having an open top end with said biocompatible liquid tank disposed within the ice water container and adapted for containing a biocompatible liquid;
   c) a biocompatible liquid infusion reservoir having an open top end with said biocompatible liquid infusion reservoir disposed within the biocompatible liquid tank, said biocompatible infusion reservoir adapted to contain a predetermined volume of biocompatible liquid;
   d) a heat exchanger and ice water pump and sprayer disposed within the ice water container, with the ice water pump and sprayer having a tubular connection to the heat exchanger;
   e) a refill pump disposed within the biocompatible liquid tank, with the refill pump having a tubular connection with the infusion reservoir, whereby said refill pump can deliver biocompatible liquid from said biocompatible liquid tank to said infusion reservoir;
   f) a return pump and a return tube disposed within the biocompatible liquid tank, with the return pump and return tube having a tubular connection with the heat exchanger;
   g) a pump assembly platform, adapted for placement upon the open top end of the biocompatible liquid tank, said platform containing an infusion pump adapted for tubular connection to the infusion reservoir, an ice water jacket pump adapted for tubular connection to an ice water supply assembly disposed within the ice water container, and a suction pump adapted for tubular connection to the biocompatible liquid tank;
   h) an insulation jacket assembly having a watertight open passage within the jacket assembly; and
   i) a tube assembly comprising a biocompatible liquid infusion tube, a biocompatible liquid suction tube, an ice water supply tube, and an ice water return tube, said infusion tube partially disposed within the passage within the jacket assembly with an open end of tube extending through a first end of the jacket assembly and adapted for a tubular connection to the infusion pump and with the other open end of the tube extending through a second end of the jacket assembly and adapted for tubular connection to an endotracheal tube, said suction tube adapted at an open end for tubular connection to the suction pump and at the other open end to the endotracheal tube, said ice water supply tube partially disposed within the passage within the jacket assembly with an open end of the tube extending through the first end of the jacket assembly and adapted for tubular connection to the ice water pump and with the other open end disposed within the passage within the jacket assembly, and said ice water return tube adapted at an open end for tubular connection to the passage within the jacket assembly and positioned at the other open end for returning ice water to the ice water container; and said tube assembly further comprising a manually compressible air bag adapted for tubular connection to an oxygen supply source and to the endotracheal tube, whereby said ice water supply and return tubes can be utilized to circulate ice water from the ice water container within the insulation jacket assembly in order to cool the biocompatible liquid within said biocompatible liquid infusion tube that is disposed within the jacket assembly,
   whereby said apparatus can use ice water to cool the predetermined volume of biocompatible liquid and can cyclically deliver and remove the cooled predetermined volume of biocompatible liquid to and from the lungs of the mammal, while allowing the use of the manually compressible air bag to supply oxygen breaths to the lungs during the delivery of the biocompatible liquid to the lungs, with said apparatus capable of cooling the mammal at a rate of approximately 4.0° C. within approximately 5 minutes.

2. The apparatus of claim 1 in which the biocompatible liquid is a perfluorocarbon.

3. The apparatus of claim 1 in which the end of the infusion tube that extends through the second end of the insulation jacket has a tubular connection to an end of a tubular "Y" fitting, with another end of the fitting having a tubular connection to the endotracheal tube and with another end of the fitting having a tubular connection to the suction tube.

4. The apparatus of claim 1 in which the infusion, suction and ice water pumps are disposed on a slideable pump tray, which can be slid across the open top end of the biocompatible liquid tank, thereby creating an opening for access to the inside of the tank.

5. The apparatus of claim 1 in which the biocompatible liquid reservoir is adapted for the insertion of a plurality of volume displacement tabs for varying the volume of biocompatible liquid contained within the reservoir, with the number of displacement tabs depending on the weight of the mammal receiving the biocompatible liquid.

6. The apparatus of claim 1 in which the biocompatible liquid reservoir contains a pair of liquid level sensors for sensing a level of the biocompatible liquid within the reservoir.

7. The apparatus of claim 1 further comprising a tube having a tubular connection at an open end to the biocompatible liquid tank and with the other open end of the tube disposed within the tank, and comprising a pump manifold having an open chamber containing the return pump and having a vertical return pipe, with the bottom end of the pipe in tubular connection with the chamber and the open top end of the pipe positioned within the tank such that it is disposed below the open end of the tube, whereby warmed biocompatible liquid returning from the lungs of the mammal can be delivered to the heat exchanger, where the liquid is cooled, before returning the liquid to the biocompatible liquid tank.

8. The apparatus of claim 1 in which the ice water container has a hinged lid containing a control panel, power source and electric circuit, which are in operable connection with the pumps.

9. The apparatus of claim 8 in which the ice water container is releasably mounted to a storage container.

10. The apparatus of claim 9 in which the storage container is releasably connected to a wheeled frame.

11. The apparatus of claim 9 in which the pump assembly and tube assembly are disposed within the storage container.

12. The apparatus of claim 9 in which the exterior dimensions of the ice water container and of the storage container are each not greater than 25 inches by 19 inches by 14 inches so as to enable the container to be transported on commercial aircraft.

13. A method of heat exchange in the lungs of a mammal by cyclically delivering and removing a biocompatible liquid to and from the lungs, comprising the following steps:

cooling a first volume of biocompatible liquid;

collecting a second volume of biocompatible liquid from the first volume of cooled biocompatible liquid with said second volume based upon the weight of the mammal;

starting the continuous delivery of the second volume of the biocompatible liquid to the lungs of the mammal;

supplying a volume of oxygen to the lungs of the mammal manually while delivering the second volume of biocompatible liquid to the lungs;

terminating the delivery of the second volume of biocompatible liquid to the lungs of the mammal within approximately 3.5 seconds after starting the delivery of said liquid;

starting the continuous removal of the second volume of the biocompatible liquid and gas from the lungs of the mammal as soon as the delivery of the liquid has been terminated; and terminating the removal of the second volume of biocompatible liquid and gas from the lungs of the mammal within approximately 4.5 seconds after starting-the removal of said liquid and gas, whereby said method is capable of cooling the mammal at a rate of approximately 4° C. within approximately 5 minutes.

* * * * *